United States Patent
Lubitz

(10) Patent No.: US 9,415,017 B2
(45) Date of Patent: Aug. 16, 2016

(54) BACTERIAL GHOSTS FOR MEDIATING INNATE IMMUNITY

(76) Inventor: Werner Lubitz, Klosterneuburg/Kritzendorf (AT)

(*) Notice: Subject to any disclaimer, the term of this patent is extended or adjusted under 35 U.S.C. 154(b) by 0 days.

(21) Appl. No.: 13/197,871

(22) Filed: Aug. 4, 2011

(65) Prior Publication Data

US 2012/0034268 A1 Feb. 9, 2012

Related U.S. Application Data

(60) Provisional application No. 61/371,302, filed on Aug. 6, 2010.

(51) Int. Cl.

| | | |
|---|---|---|
| C12Q 1/00 | (2006.01) |
| C12Q 1/68 | (2006.01) |
| C12N 1/12 | (2006.01) |
| G01N 33/53 | (2006.01) |
| A61K 9/50 | (2006.01) |
| A61K 31/05 | (2006.01) |
| A61K 38/20 | (2006.01) |
| A61K 45/06 | (2006.01) |
| A61K 39/39 | (2006.01) |
| A61K 39/00 | (2006.01) |

(52) U.S. Cl.
CPC .......... *A61K 9/5068* (2013.01); *A61K 31/05* (2013.01); *A61K 38/204* (2013.01); *A61K 38/2046* (2013.01); *A61K 39/39* (2013.01); *A61K 45/06* (2013.01); *A61K 2039/55594* (2013.01)

(58) Field of Classification Search
CPC ... A61K 35/74; A61K 48/00; A61K 49/0097; A61K 38/164; A61K 2039/6006; A61K 2035/11; C12N 15/03; C12N 15/67; C12N 15/70; C12N 15/74; C12N 15/79; C12N 1/00
See application file for complete search history.

(56) References Cited

FOREIGN PATENT DOCUMENTS

| | | |
|---|---|---|
| CN | 101658668 A | 3/2010 |
| EA | 007792 B1 | 2/2007 |

OTHER PUBLICATIONS

Ekong et al., FEMS Immunology & Medical Microbiology. vol. 55. Issue 2. pp. 280-291. Mar. 2009. Article first published online Nov. 19, 2008.*
Mayr et al., (Infection & Immunity. Aug. 2005. vol. 73(8): 4810-4817).*
Koller. Dissertation: Bacterial Ghosts as Carriers of Active Substances: Effects on Cell Viability and Induction of Innate Immunity. Published May 29, 2010. Mag. Verena Juliana Koller. Universitat wien.*
Bacterial ghosts as carrier of active substances: Effects . . . —E-Theses http://othes.univie.ac.at/10364/.*
Eko et al., (J. of Immunol. 2004. vol. 173(3): 3375-3382).*
Oppenheim et al., (Ann Rheum Dis. 2003. vol. 62, Issue Suppl 2. pp. ii17-ii21).*
Mayr et al., (Infect. And Immun. 2005. vol. 73(8); 4810-4817.*
Schroder et al., (J. of Leukocyte Biology. 2004. vol. 75. No. 2:163-189).*
Tomasinsig et al., ( J. Leukoc. Biol. Nov. 2002: 72(5):1003-10).*

(Continued)

*Primary Examiner* — Ja'na Hines
(74) *Attorney, Agent, or Firm* — Rothwell, Figg, Ernst & Manbeck, P.C.

(57) ABSTRACT

The invention relates to the use of bacterial ghosts (BG) to promote an innate immune response.

18 Claims, 9 Drawing Sheets

(56) References Cited

OTHER PUBLICATIONS

Figure 1:
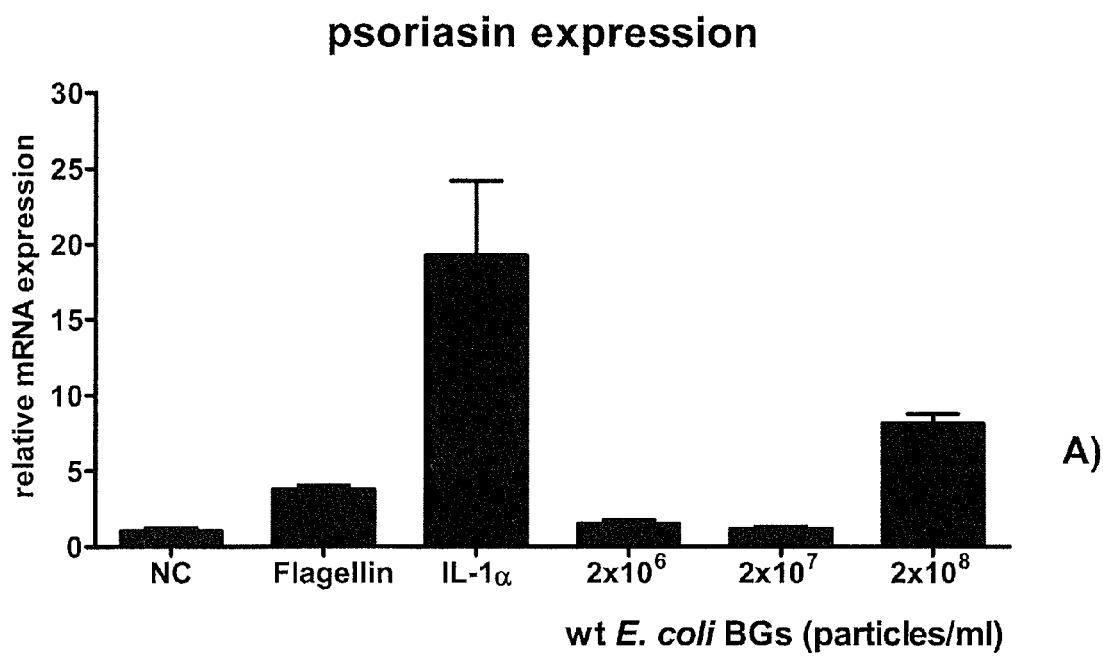

Lubitz Petra et al: "Applications of Bacterial Ghosts in Biomedicine", Pharmaceutical Biotechnology Springer-Verlag Berlin, Heidelberger Platz 3, D-14197 Berlin, Germany Series: Advances in Experimental Medicine and Biology (ISSN 0065-2598(Print)), 2009, pp. 159-170, XP008145631, cited in the application abstract p. 167, paragraph 3-p. 168, paragraph 3.

Bochau Amanda S et al: "S100A15, an antimicrobial protein of the skin: regulation by *E. coli* through Toll-like receptor 4.", The Journal of Investigative Dermatology Nov. 2007 LNKD-PUBMED:17625598, vol. 127, No. 11, Nov. 2007, pp. 2596-2604, XP002664207, ISSN: 1523-1747 the whole document.

Falchetti R et al: "Effects of resveratrol on human immune cell function.", Life Sciences Nov. 21, 2001 LNKD-PUBMED:11764009, vol. 70, No. 1, Nov. 21, 2001, pp. 81-96, XP002664208, ISSN: 0024-3205 cited in the application abstract.

Abtin A et al: "*Escherichia coli* ghosts promote innate immune responses in human keratinocytes", Biochemical and Biophysical Research Communications 2010 Academic Press Inc. USA LNKD-DOI:10.1016/J.BBRC2010.08.013, vol. 400, No. 1, Sep. 2010, pp. 78-82, XP27275784, ISSN: 0006-291X the whole document.

Abtin et al., "Flagellin is the principal inducer of the antimicrobial peptide S100A7c (psoriasin) in human epidermal keratinocytes exposed to *Escherichia coli*", The FASEB Journal, Research Communication, (2008), vol. 22, pp. 2168-2176. (cited in the current specification).

Banyer et al., "Cytokines in Innate and adaptive immunity", Rev. Immunogenetics, (2000), vol. 2, pp. 359-373.

Glaser et al., "Antimicrobial psoriasin (S100A7) protects human skin from *Escherichia coli* infection", Nature Immunolgy, (2005), vol. 6, pp. 57-64. (cited in the current specification).

Iovine et al., "Reactive Nitrogen Species Contribute to Innate Host Defense against Campylobacter jejuni", Infection and Immunity (2008), vol. 76, No. 3, pp. 986-993.

Mogensen et al., "Pathogen Recognition and Inflammatory Signaling in Innate Immune Defenses", Clin. Microbiol. Rev., (2009), 22 (2): 240-273.

Kudela et al., "Bacterial ghosts (BGs)—Advanced antigen and drug delivery system", Vaccine 28 (2010) 5760-5767.

Riedmann et al., "Bacterial ghosts as adjuvant particles", Expert Rev. Vaccines, Apr. 2007; 6(2), pp. 241-253.

Schultz, "Clinical use of *E.coli* Nissle 1917 in inflammatory bowel disease", Inflamm Bowel Dis., 2008, (7), pp. 1012-1018.

* cited by examiner

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: B2M forward primer

<400> SEQUENCE: 1
gatgagtatg cctgccgtgt g                                            21

<210> SEQ ID NO 2
<211> LENGTH: 19
<212> TYPE: DNA
<213> ORGANISM: Artificial Sequence
<220> FEATURE:
<223> OTHER INFORMATION: B2M reverse primer

<400> SEQUENCE: 2

```
caatccaaat gcggcatct                                                    19

<210> SEQ ID NO 3
<211> LENGTH: 22
<212> TYPE: DNA
<213> ORGANISM: Artificial Sequence
<220> FEATURE:
<223> OTHER INFORMATION: psoriasin forward primer

<400> SEQUENCE: 3
ggagaacttc cccaacttcc tt                                                22

<210> SEQ ID NO 4
<211> LENGTH: 23
<212> TYPE: DNA
<213> ORGANISM: Artificial Sequence
<220> FEATURE:
<223> OTHER INFORMATION: psoriasin reverse primer

<400> SEQUENCE: 4
ggagaagaca ttttattgtt cct                                               23
```

BACTERIAL GHOSTS FOR MEDIATING INNATE IMMUNITY

This application is a non-provisional of U.S. Ser. No. 61/371,302 filed Aug. 6, 2010, the disclosure of which is incorporated herein in its entirety by reference.

DESCRIPTION

1. Field of the Invention

The invention relates to the use of bacterial ghosts (BG) to promote an innate immune response.

2. Background Art

The immune system protects an organism against disease by identifying and killing pathogens, such as bacteria, viruses and parasitic worms, as well as tumor cells. In order to recognize and neutralize pathogens multiple mechanisms evolved. The typical vertebrate immune system comprises several lines of defense of increasing specificity. Most simply, physical barriers prevent pathogens from entering the organism. If a pathogen breaches these barriers, the innate immune system provides an immediate, but non-specific response. If pathogens successfully evade the innate immune response, vertebrates possess a third layer of protection, the adaptive immune system which is activated by the innate immune response. Here the immune system adapts its response during an infection to improve its recognition of the pathogen. This improved response is then retained after the pathogen has been eliminated, in the form of an immunological memory, and allows the adaptive immune system to react faster and stronger each time this pathogen is encountered. Said immunological memory is also the principle underlying immunization. In the context of the present invention the innate immune system is of particular interest.

The innate immune system serves to protect a host from invading microorganisms in a non-specific manner. Upon activation, e. g. by phagocytosis of bacteria, viruses or protozoa by macrophages, monocytes, neutrophils and dentritic cells, the innate immune system triggers a series of host defense responses (Akira et al., 2006. Cell 124:783-801). A central mechanism of these responses is the production and/or release of pro-inflammatory cytokines, antimicrobial defense molecules, hydrolytic enzymes, reactive oxygen species (ROS) or reactive nitrogen species (RNS). Different components of microbial pathogens, referred to as pathogen-associated molecular patterns (PAMPs), are recognized by pattern recognition receptors (PRRs) of the innate immune system. Among these receptors are the Toll-like receptors (TLRs), NOD-like receptors (NLRs), RIG-like receptors (RLRs) and peptidoglycan-like recognition proteins (PGRPs), all contributing to early host defense against pathogens (Creagh and O'Neill. 2006. Trends Immunol. 27:352-357; Dziarski and Gupta. 2006. Cell Microbiol. 8:1059-1069; Ishii et al., 2008. Cell Host. Microbe 3:352-363). For example, the bacterial PAMP flagellin, a monomer subunit of the flagellum, binds to TLR5 and activates the transcription factor NF-kappaB (Hayashi et al., 2001. Nature 410:1099-1103) ultimately leading to the expression of pro-inflammatory cytokines and antimicrobial peptides including psoriasin (S100A7c) and human β-defensin 2 (hBD-2) in human primary keratinocytes (KCs) (Abtin et al., 2008. FASEB J. 7:2168-2176; Akira, and Takeda. 2004. Nat. Rev. Immunol. 4:499-511; Miller et al., 2005. J. Immunol. 174:6137-6143).

It has been reported that *E. coli* cell culture supernatants or disrupted cells of *E. coli* strains induce and/or enhance the expression of the antimicrobial peptides psoriasin and hBD-2 in epidermal KCs (Abtin et al., 2008. FASEB J. 7:2168-2176; Glaser et al., 2005. Nat. Immunol. 6:57-64.). Said response is triggered by fragments of cells. As reported earlier, the responsiveness towards *E. coli* by KCs is mediated through TLR5 and its ligand flagellin (Abtin et al., 2008. FASEB J. 7:2168-2176).

It was an object of the present invention to enhance the innate immune defence system, in particular the innate immune defence system of the skin. Therefore, the expression of innate immune modulators should be stimulated.

Therefore, in one aspect, the present invention relates to the use of bacterial ghosts (BG) to promote the innate immune response.

According to the present invention, it was surprisingly found that the envelope structure of bacterial ghosts (BGs) is recognized by KCs and promotes innate immune responses. In particular, it has been found that an innate immune response can be promoted by bacterial ghosts having a native or almost native envelope structure.

BGs are non-living cell envelope preparations from bacteria, in particular from Gram-negative bacteria, devoid of cytoplasmic contents. BGs can, e. g., be produced by the controlled expression of a plasmid-encoded lysis gene in bacteria, e. g. by expression of plasmid encoded lysis gene E of bacteriophage φX174 in Gram-negative bacteria. Gene E codes for a membrane protein, which is able to fuse inner and outer membranes and thus forming an E-specific lysis tunnel through which all the cytoplasmic content is expelled (Witte et al., 1990. Biochimie 72:191-200; Witte et al., 1990. J. Bacteriol. 172:4109-4114). BGs being non-living bacterial envelopes maintain the full cellular morphology of the native bacteria. All the cell surface structures, including the outer membrane proteins, adhesins, lipopolysaccharide (LPS) and peptidoglycan are preserved in BGs (Mayr et al., 2005. Adv. Drug Deliv. Rev. 57:1381-1391).

It has been shown previously that BGs are capable of stimulating the adaptive immune system. In particular, BGs can be used for immunization either against their own envelope structure or as an antigen delivery system for foreign target antigens (Jalava et al., 2003. Expert. Rev. Vaccines. 2:45-51; Mayr et al., 2005. Adv. Drug Deliv. Rev. 57:1381-1391). Immunization with *Vibrio cholerae* ghosts protects against diarrhea and death following challenge with fully virulent *V. cholerae* in a rabbit animal model (Eko et al., 2003. Vaccine 21:3663-3674) or incorporation of a core antigen of hepatitis B virus on the surface of *E. coli* BGs results in a significant immune response against this core antigen in mice (Jechlinger et al., 2005. Vaccine 23:3609-3617). BGs can also be used as delivery vehicles for active substances such as doxorubicin (Paukner et al., 2006. Expert. Opin. Drug Deliv. 3:11-22) or as a carrier of DNA (Kudela et al., 2007. Cancer Lett. 1:54-63) and enzymes (Huter et al., 1999. Journal of Controlled Release 61:51-63.).

In the present invention bacterial ghosts were found to enhance also the innate immune defence system, in particular the innate immune defence system of the skin. Therefore, bacterial ghosts (BG) were used to promote the innate immune response.

In a preferred embodiment of the invention the surface of the bacterial ghosts does not comprise flagellin monomers.

In another preferred embodiment the surface of the bacterial ghosts does not comprise flagellin.

Flagellin is a protein of about 30,000 to 60,000 daltons which polymerizes to form the filament of the bacterial flagellum. The protein flagellin is the principal substituent of the bacterial flagellum, and is present in large amounts on nearly all flagellated bacteria. In mammals adaptive immune responses, i.e. T cell and antibody responses, are frequently raised to flagellar antigens and, thus, to flagellated bacteria. This is probably due to the fact that flagellin is an extremely abundant protein in flagellated bacteria, and further a specific innate immune receptor exists that recognizes flagellin, TLR5.

Bacterial ghosts which do not comprise flagellin on the surface may be derived from a bacterial strain that is not able to express flagellin, e. g. a flagellin deletion mutant. Alternatively, said bacterial ghosts may be derived from a bacterial strain that is not able to transport flagellin to the cell surface. In order to obtain bacterial ghosts which do not comprise flagellin on the surface any suitable method of genetic engineering known in the art can be used. For example, deletion of the gene encoding the flagellin protein results in a flagellin deletion mutant. Alternatively, the expression of flagellin may be suppressed by any suitable method known in the art, e. g. using RNAi. Further, a mutation, e. g. a premature stop codon, may be introduced into the gene encoding the flagellin protein resulting in the expression of a truncated protein. Deletion and/or mutation of expression control sequences of the flagellin gene may also lead to loss of function of the gene and may thus result in a bacterial strain that is not able to express flagellin. A mutant bacterial strain that is not able to transport flagellin to the cell surface may also be obtained, e. g. by deletion and/or mutation of the respective sequence of the flagellin gene. Said techniques are well-known to those skilled in the art.

Knowing that flagellin is a bacterial component important for the stimulation of both, the innate as well as the adaptive immune response, it was even more surprising that BGs devoid of flagellin are also effective at promoting innate immune responses.

The innate immune response is preferably promoted by induction of the expression and/or release of at least one innate immune modulator.

Immune modulators participate in the adjustment of the immune response to a desired level, such as in immunopotentiation, immunosuppression, or induction of immunological tolerance. Immunopotentiation, i. e. enhancement of the immune response, is desired according to the invention. The immune response may be enhanced by increasing the speed and extent of its development and by prolonging its duration.

Innate immune modulators are immune modulators, as defined above, which are involved in the innate immune response. Examples of innate immune modulators include pro-inflammatory cytokines, reactive nitrogen species (RNS) and reactive oxygen species (ROS).

According to the invention it is preferred that the expression and/or release of at least one innate immune modulator selected from the group consisting of antimicrobial defense molecules, pro-inflammatory cytokines, reactive nitrogen species (RNS) and reactive oxygen species (ROS) is induced.

Antimicrobial defense molecules, also known as antimicrobial peptides or host defence peptides, are potent, broad spectrum antibiotics. Said molecules have been demonstrated to kill Gram-negative and Gram-positive bacteria, mycobacteria, enveloped viruses, fungi and even transformed or cancerous cells. Unlike the majority of conventional antibiotics antimicrobial peptides may also have the ability to enhance immunity by functioning as immunomodulators. Examples of antimicrobial defense molecules include psoriasin and human β defensin-2 (hBD-2).

According to the invention the expression of at least one antimicrobial defense molecule, selected from the group consisting of psoriasin and human β defensin-2 (hBD2-) is enhanced.

Pro-inflammatory cytokines are cytokines that promote systemic inflammation. Examples of pro-inflammatory cytokines include TNF-alpha, interleukin-1 (IL-1), interleukin-6 (IL-6) and interleukin-8 (IL-8).

According to the invention the expression and/or release of at least one pro-inflammatory cytokine selected from the group consisting of interleukin-6 (IL-6) and interleukin-8 (1-8) is enhanced.

Reactive nitrogen species (RNS) are a family of antimicrobial molecules derived from nitric oxide (NO) and superoxide ($O^{2-}$) produced via the enzymatic activity of inducible nitric oxide synthase (iNOS) and NADPH oxidase, respectively. iNOS is expressed primarily in macrophages after induction by cytokines and microbial products, notably interferon-gamma (IFN-γ) and lipopolysaccaride (LPS). However, generation of nitric oxide (NO) is not only a feature of phagocytes. Also other cells that are involved in immune reactions, e.g. epithelial cells or keratinocytes, are capable of producing these radicals (Bogdan, C., 2001. Nat Immunol 2(10): p. 907-16; Bogdan, C., 2000 Immunol Rev. 173: p. 17-26; Bogdan et al., 2000 Curr Opin Immunol. 12(1): p. 64-76).

NO has been shown to be a versatile molecule, exhibiting an ambiguous enodogenous role, with a rapid half-life of approximately 6 s (Sharma et al., 2007. Inflammopharmacology 15(6): p. 252-9). On the one hand it represents a crucial mediator molecule for various cellular functions, but when produced in excessive amounts, such as under oxidative burst conditions, it can cause cytotoxic and mutagenic effects (Sharma et al., 2007. Inflammopharmacology 15(6): p. 252-9).

As NO acts as an antimicrobial agent, it is absolutely essential for fighting intracellular pathogens, such as *Salmonella enterica, Trypanosoma musculi, Mycobacterium tuberculosis, Legionella pneumophila* or *Leishmania major* (Chakravortty and Hensel, 2003. Microbes Infect. 5(7): p. 621-7; Summersgill et al., 1992 J Leukoc Biol. 52(6): p. 625-9).

The highly reactive NO is implicated in the pathophysiology of many diseases. However, due to various effector and immunoregulatory functions, e.g. antimicrobial, antitumorigenic and apoptotic activity or its modulating character of cytokines and T cell differentiation, NO plays an important role in the immune system. Low concentrations of NO are contributed to antimicrobial activity against certain bacterial pathogens but high concentrations are found to play roles in inflammation and carcinogenesis. Actually, there are three major nitric oxide synthase (NOS) isoforms known; the constitutively expressed neuronal NOS (also known as nNOS or NOS1) and endothelial NOS (eNos or NOS3) as well as the inducible isoform (iNOS or NOS2). The latter is accountable for the NO-production in macrophages and keratinocytes. All three types of NOS oxidize one molecule of L-arginine at a guanidine nitrogen to an intermediate which is oxidized to yield one molecule of NO and L-citrulline (Bogdan, C., 2001. Nat Immunol 2(10): p. 907-16; Bogdan, C., 2000 Immunol Rev. 173: p. 17-26; Bogdan et al., 2000 Curr Opin Immunol. 12(1): p. 64-76; Sharma et al., 2007. Inflammopharmacology 15(6): p. 252-9).

Bacterial lipopolysaccaride (LPS) is among the most important stimuli for iNOS induction. A macrophagic sensor of conserved bacterial components is represented by TLR4 which is able to trigger the innate immune system via binding of its main agonist LPS (Ishii et al., 2008 Cell Host Microbe. 3(6): p. 352-63).

Binding sites for transcription factors like for NFkappa b are found in the promoter region of the iNOS gene. Its activation upon exposure of macrophages to LPS gives rise to an enhanced expression (Bogdan et al., 2000 Curr Opin Immunol. 12(1): p. 64-76).

According to the invention the release of at least one reactive nitrogen species, e. g. NO, is enhanced.

Reactive oxygen species (ROS) are free radicals that contain the oxygen atom. They are highly reactive due to the presence of unpaired valence shell electrons. ROS form as a natural byproduct of the normal metabolism of oxygen and have important roles in cell signaling. However, during times of environmental stress (e.g. UV or heat exposure) ROS levels can increase dramatically, which can result in significant damage to cell structures. This cumulates into a situation known as oxidative stress.

According to the invention the release of at least one reactive oxygen species is enhanced.

Reactive nitrogen species act together with reactive oxygen species (ROS) to damage cells, causing nitrosative stress. Therefore, these two species are often collectively referred to as ROS/RNS.

In another preferred embodiment of the invention, a further active agent, e. g. a drug and/or other biological substance, may be administered in combination with the bacterial ghosts. Said active agent may be added to the bacterial ghosts so that the active agent is substantially incorporated into the bacterial ghosts. Alternatively, the active agent is simply present aside the bacterial ghosts. The active agent may be an immunomodulator, i. e. a drug and/or substance that is suitable to enhance the immune system, in particular a drug and/or substance which exhibits an effect on the innate immune system, the adaptive immune system, or both. Alternatively said active agent may be any other pro-drug or drug. The person skilled in the art knows a variety of suitable pro-drugs and drugs. A particular active agent for use with the bacterial ghosts will be determined considering the specific situation of the person receiving the bacterial ghosts in order to stimulate his/her innate immune system. The active agent may also be an antioxidant, such as a polyphenol, e. g. resveratrol.

Resveratrol is a polyphenolic compound, naturally occurring either in trans- or cis-isomeric forms in various plant species, especially present in skins of grapes, peanuts and berries showing a broad spectrum of immunomodulating activities. Many studies allocate anticancer, antioxidant and cardioprotective properties as well as an extended life-span of various organisms to it (Aggarwal et al., 2004. Anticancer Res. 24(5A): p. 2783-840; Gao et al., 2003. Biochem Pharmacol. 66(12): p. 2427-35; Falchetti et al., 2001. Life Sci. 70(1): p. 81-96; Saiko et al., 2008. Mutat Res. 658(1-2): p. 68-94). Moreover, resveratrol possesses great therapeutic potential in treatment of a variety of infectious diseases of animals and humans. Its activity has been demonstrated against dermatophytes (Chan, 2002. Biochem Pharmacol. 63(2): p. 99-104) and viruses like Herpes simplex (Faith et al., 2006. Antiviral Res. 72(3): p. 242-51). The growth inhibitory effect of resveratrol has been substantiated for a broad range of bacterial species including intracellular *Chlamydia pneumoniae* that accounts for acute respiratory tract infections (Chan, 2002. Biochem Pharmacol. 63(2): p. 99-104; Schriever et al., 2003 Atherosclerosis. 171(2): p. 379-80). Furthermore, decreased infectivity of protozoa species which cause diseases in fish (Leiro et al., 2004 Dis Aquat Organ. 59(2): p. 171-4; Leiro et al., 2004 Antimicrob Agents Chemother. 48(7): p. 2497-501) was achieved and more recently the elimination of the intracellular skin pathogen *L. major*, responsible for cutaneous leishmaniasis, by resveratrol was demonstrated (Kedzierski et al., 2007. Parasitol Res. 102(1): p. 91-7; Kedzierski et al., 2009. Curr Med Chem. 16(5): p. 599-614).

The bacterial ghosts used according to the invention may be derived from a variety of bacteria. Preferably the bacterial ghosts are derived from apathogenic Gram-negative bacteria, more preferably from an *E. coli* strain. Any *E. coli* strain may be used. An example of a suitable *E. coli* strain is *E. coli* Nissle 1917.

As outlined above, surface barriers, such as the skin, are examples of the mechanical barriers that are the first line of defense against infection. Further, the skin and respiratory tract secrete antimicrobial peptides, e. g. β-defensins, and thus function as chemical barriers protecting against infection. Therefore, the innate immune response is preferably promoted in the skin and/or mucosa, which is also termed mucous membrane. Examples of mucosa include oral, buccal, esophageal, gastric, intestinal, respiratory, bronchial, nasal, olfactory, uterine, penile mucosa and the endometrium.

The skin as well as the mucosa consist of epithelial cells. Epithelial cells form an epithelium, which represents a tissue composed of cells that line the cavities and surfaces of structures throughout the body.

Keratinocytes are the major constituents of the epidermis, i. e. the outer layer of the skin. Keratinocytes are essential immunomodulaters, maintaining the intergrity of the immune response by secreting inhibitory cytokines such as IL-4 and TGFβ when dormant, but when provoked, the keratinocytes will stimulate cutaneous inflammation and Langerhans cell activation via TNFα and IL-1β secretion.

According to the invention, the expression and/or release of the at least one innate immune modulator is preferably induced in epithelial cells. Preferably, the epithelial cells are keratinocytes.

Stimulation of the innate immune response is believed to enhance the defense of the host against infection by other organisms, in a non-specific manner. Therefore, according to the invention, it is preferred that the innate immune response is promoted in mammals, preferably in humans, more preferably in individuals susceptible to infection or individuals with compromised immune system.

In a further aspect of the invention, the bacterial ghosts are administered to a mammal, preferably a human. It is preferred that the bacterial ghosts are administered to the skin and/or mucosa.

Suitable modes of administration of bacterial ghosts include oral, topical, mucosal, nasal and/or pulmonal administration.

Suitable pharmaceutical formulations are in the form of, e. g. a gum, inhaler, nasal spray, dermal patch, ointment, lotion, aerosol, suppository, irrigation, gel liquid, suspension, tooth paste.

According to the invention, it is possible to administer bacterial ghosts to any individual. Preferably, bacterial ghosts are administered to babies, young children, elderly, chronically sick individuals, individuals with compromised immune system, e. g. AIDS patients, graft recipients.

In a further aspect, the invention relates to a method of promoting an innate immune response, wherein bacterial ghosts (BG) are administered to a patient. Suitable modes of administration of bacterial ghosts and suitable pharmaceutical forms/dosage forms/formulations are as described above.

FIGURES

FIG. 1. BGs induce the expression of antimicrobial psoriasin in human primary KCs. KCs were incubated for 24 h with flagellin (10 ng/ml), IL-1α (10 ng/ml), wt *E. coli* BGs varying from $2\times10^6$ to $2\times10^8$ particles/ml or without stimulation (NC), thereafter total RNA was isolated and reverse-transcribed to cDNA. The relative expression of antimicrobial psoriasin was determined by qRT-PCR. The mean values are displayed in relation to untreated cells (NC). Relative gene expression levels were normalized to the expression of the housekeeping gene β-2-microglobulin. Data represent the mean±SD of triplicate samples.

Figure 2:
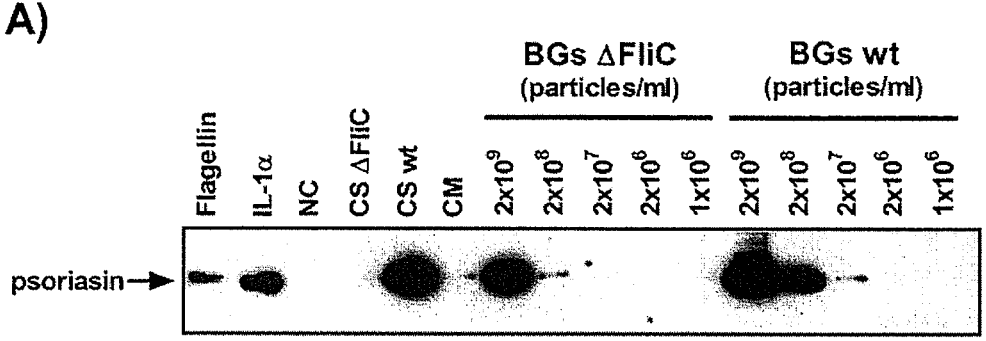
Figure 2:
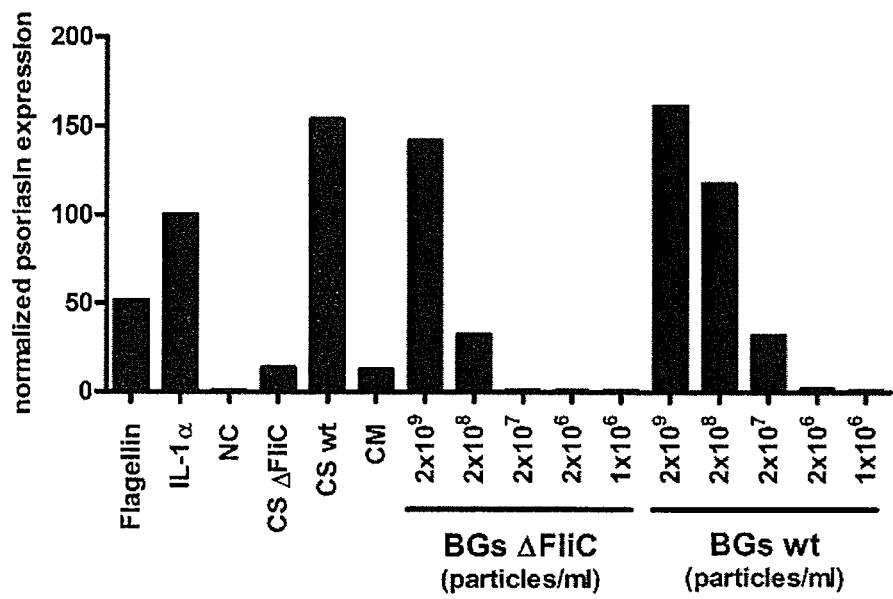

FIG. 2. Induction of psoriasin in KCs by wt and ΔFliC *E. coli* BGs. KCs were incubated for 48 h with wt and ΔFliC *E. coli* BGs from $1\times10^6$ to $2\times10^9$ particles/ml. Stimulation with flagellin (10 ng/ml), IL-1α (10 ng/ml), non-stimulated cells (NC), non-conditioned bacterial culture medium (CM), and culture supernatants of wt *E. coli* (CS wt) and ΔFliC *E. coli* (CS ΔFliC) were used as controls. 48 h after stimulation the cell lysates from KCs were subjected to immunoblot analysis for psoriasin production (A). Quantification of immunoblot of psoriasin protein expression (A) by densitometric analysis normalized to IL-1α stimulation of KCs (B). One representative experiment of three performed is depicted.

Figure 3:
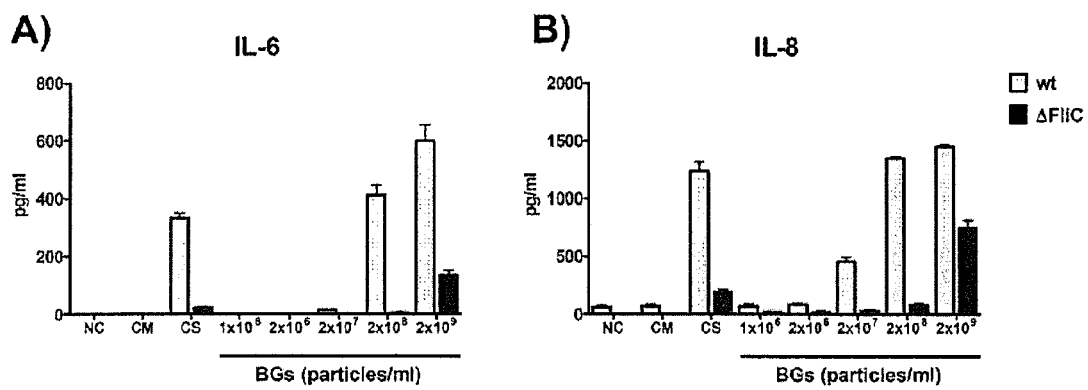

FIG. 3. BGs induce the secretion of pro-inflammatory cytokines. KCs were incubated for 48 h with wt *E. coli* and ΔFliC *E. coli* BGs from $1\times10^6$ to $2\times10^9$ particles/ml, and in the presence of culture supernatants (CS) of wt and ΔFliC *E. coli*. Non-stimulated cells (NC) and cells incubated in the presence of non-conditioned bacterial culture medium (CM) served as negative controls. After the incubation period KC's culture medium was collected and the concentrations of IL-6 (A) and IL-8 (B) were determined by ELISA. Data represent the mean±SD of three independent experiments performed in triplicates.

Figure 4:
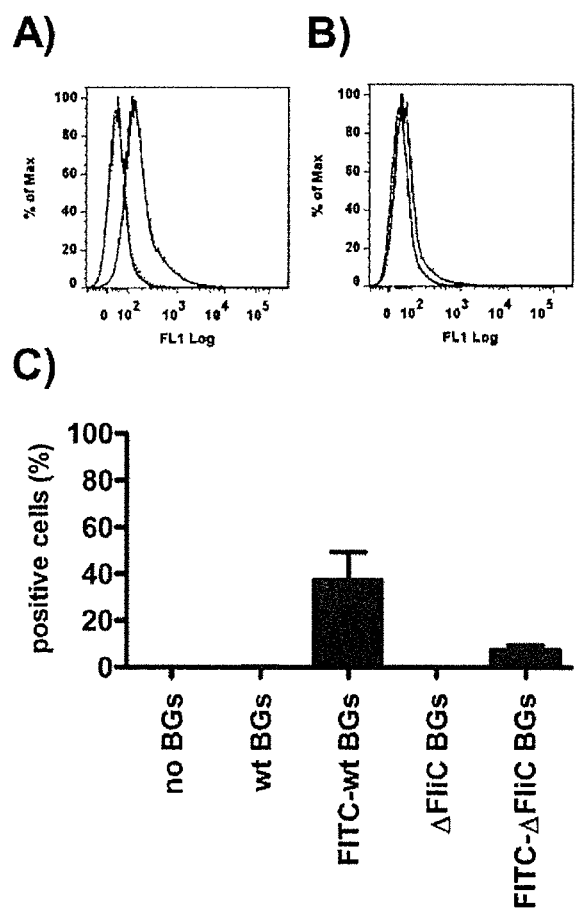

FIG. 4. Comparative flow cytometric analysis of the internalization of BGs by human primary KCs. KCs were incubated with FITC-labeled BGs ($1\times10^3$ per cell)—wt *E. coli* (A) and ΔFliC *E. coli* (B) BGs (open histogram-full line) for 2 h at +37° C. Cells incubated without BGs (shaded histogram) or with non-labeled BGs (open histogram-dotted line) served as the controls. Values were calculated as the percentage of cells with increased fluorescence incubated without or with non-labeled BGs subtracted from the percentage of positive cells incubated with FITC-labeled BGs. Each bar represents the mean of four independent experiments±SD (C).

Figure 5:
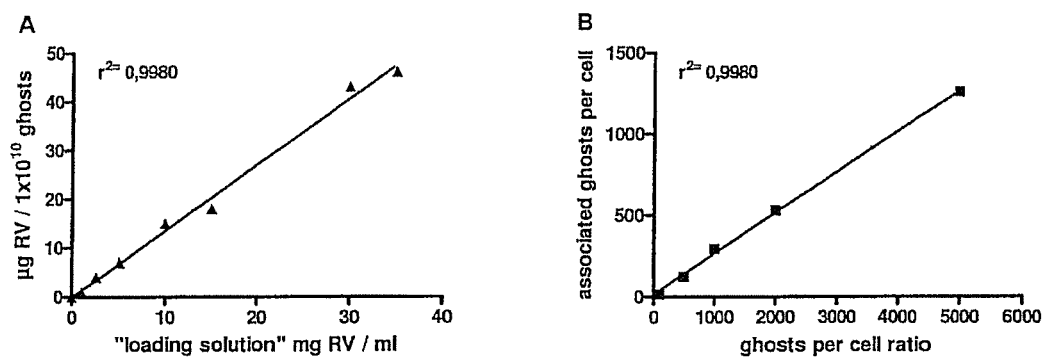

FIG. 5. Correlation between RV loading solution and recovered amount from loaded *E. coli* NM522 ghosts.

The direct correlation of the RV loading solution and the amount of RV after ethanol extraction is depicted by the linear regression. Values were obtained by HPCL measurements (A). Figure (B) depicts the linear regression between applied and associated FITC-labeled BGs after 20 min coincubation with RAW 264.7 cells. Values represent means of 4 independent measurements and were calculated as described in materials and methods.

Figure 6:
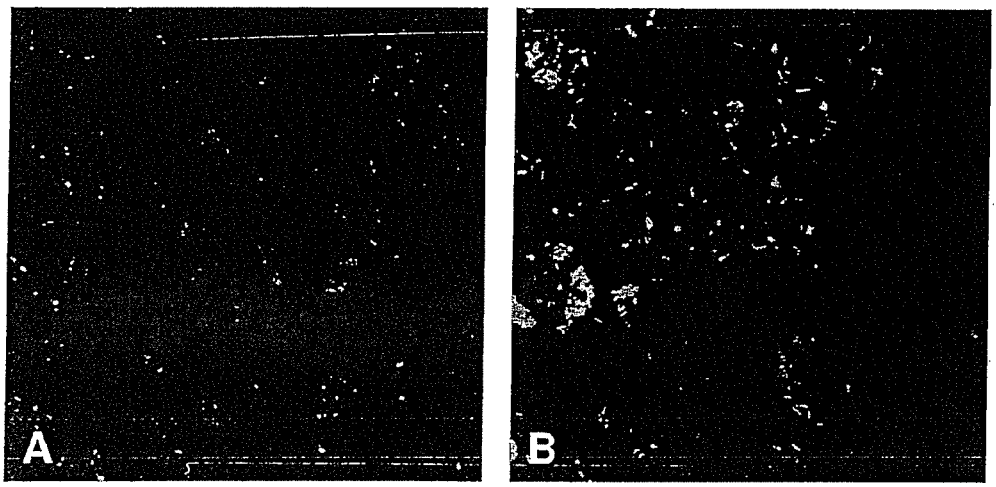

FIG. 6. Adherence and uptake of BGs by murine macrophages. Confocal laser scanning microscopy was performed after incubation of macrophages with FITC-labeled *E. coli* NM522 ghosts in a ghost to cell ratio of 1000. RAW 264.7 cells were stained with Texas-Red Phalloidin. FITC-marked BGs, located inside the cell, appear yellow and not engulfed give a green color. Images display a representative single z-stack of various optical sections. Pictures were taken with and 20-fold objective (A) after 20 min or with a 63× oil objective (B) after 40 min incubation. No image processing steps have been performed.

Figure 7:
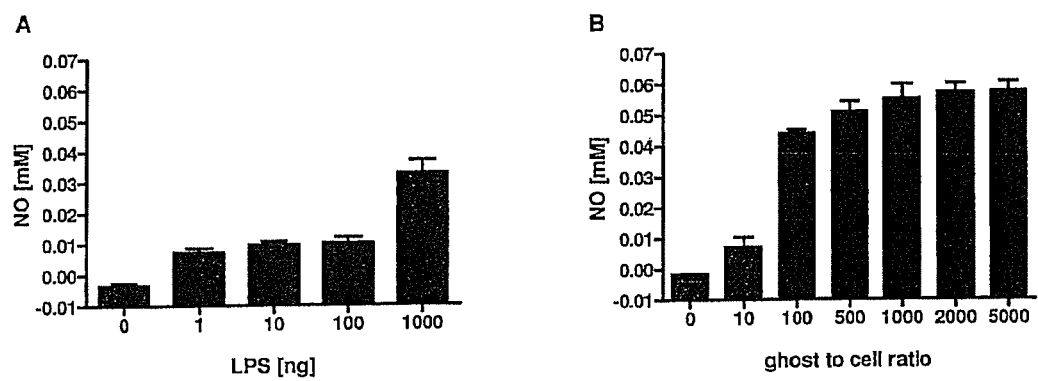

FIG. 7. Induction of NO-production. RAW 264.7 cells were treated with different LPS concentrations for 20 hours (A). Impact of various amounts of BGs on the stimulation of NO generation after 20 min treatment and 20 hours further incubation (B). A dose dependent induction can be seen until a MOI of 1000. Higher amounts did not have any further influence. Treatment was performed in the latter experiments for 20 min and after 20 hrs the NO-concentrations were determined by the Griess-assay as described in materials and methods. Bars indicate mean values+SD. Each experimental point represents values form 4 independent cultures measured in triplicate.

Figure 8:
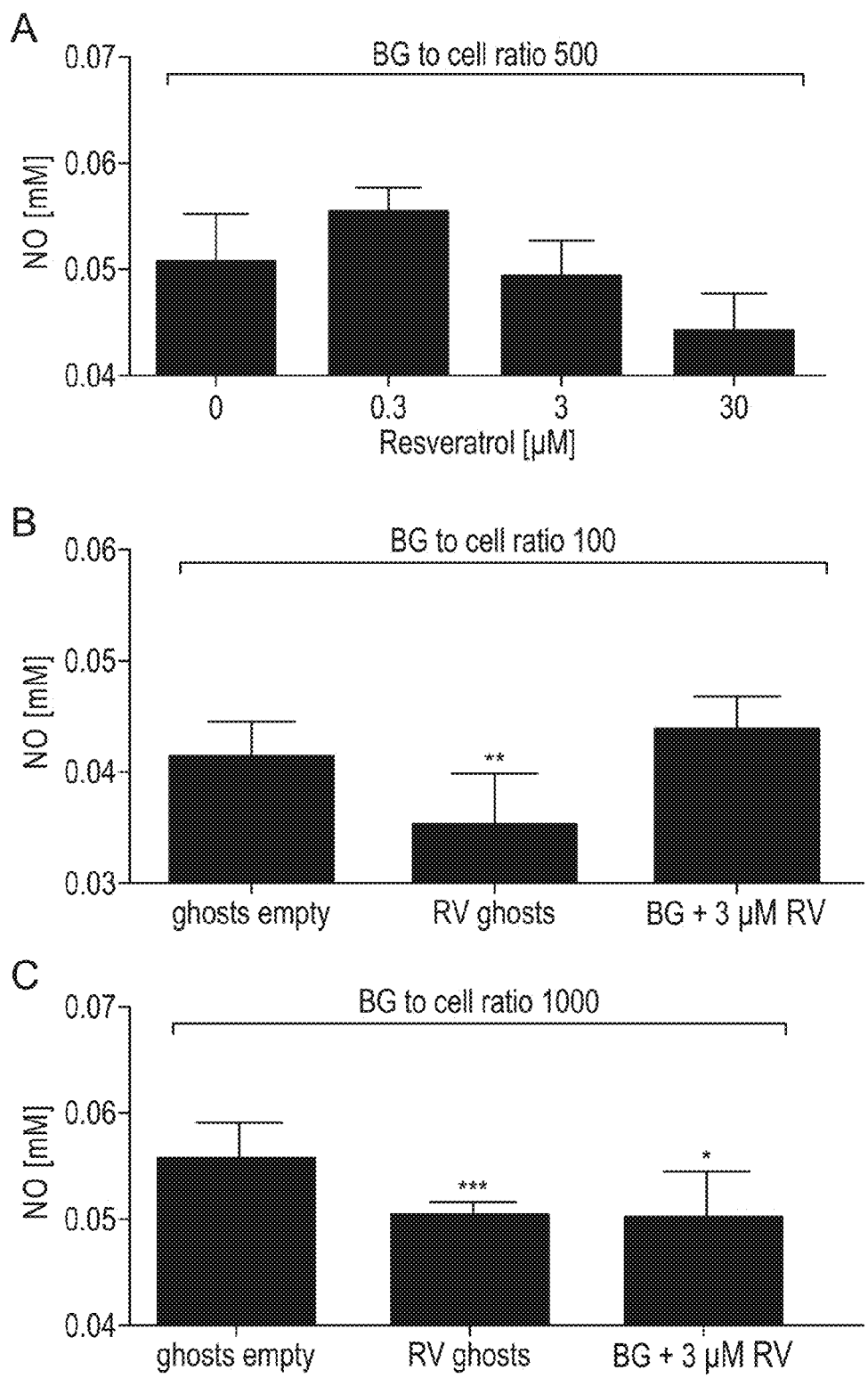

FIG. 8. Impact of RV and RV-loaded BGs on the NO production in the macrophage cell line RAW 264.7 induced by different amounts of BGs. The reduction of NO production which was induced by BGs (BG to cell ratio of 500) after simultaneous treatment with different RV concentrations is depicted (A). The reduction of NO generation after treatment in a BG to cell ratio of 100 is shown in figure (B). Highly significant decrease in NO-stimulation was found with ratios of 1000 (C). Based on the calculation from cell associated BGs, BG to cell ratios of 100 and 1000 would correspond to RV-concentrations 0.48+0.25 μM and 8.86+2.21 μM, respectively. It can be seen that BG-loaded RV reduced significantly the induction of NO-production. In comparison, externally provided RV which is approximately 6-times higher than the amount of the chemical delivered by BGs in a MOI of 100, had no impact at all. Treatment was performed in all experiments for 20 min and after 20 hrs the NO concentrations (A-C) were determined by the Griess-assay as described in materials and methods. Bars indicate mean values+SD. Each experimental point represents values from four independent cultures measured in triplicate. Asterisks indicate values which are significant different from their respective control (p<0.05). Analyses were performed with unpaired two tailed Student's t-test.

Figure 9:
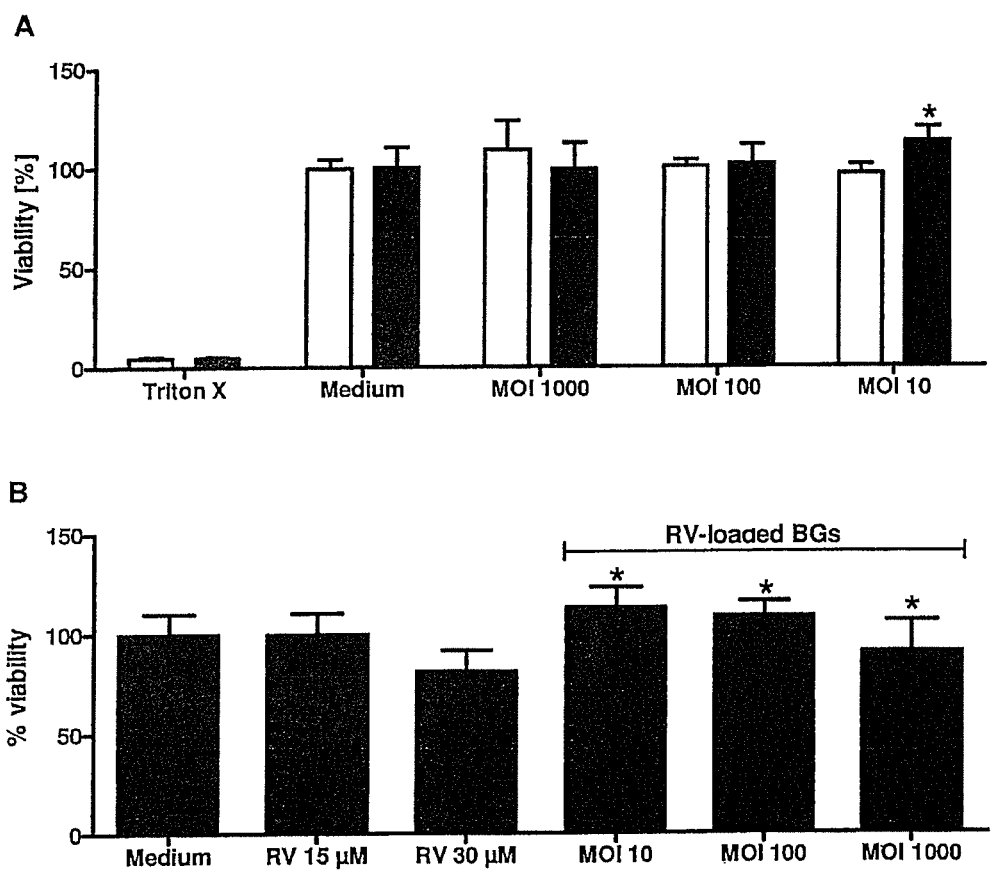

FIG. 9. Impact of empty *E. coli* NM522 BGs on the viability of RAW 264.7 macrophages (A). Cells were incubated with three different BG to cell ratios (10,100,1000) for either 20 min followed by 20 hours recovery period (white bars) or for 24 hours. Cell viability was assessed by the use of neutral red assay. The cytotoxic effects of RV in contrast to the implication of RV-loaded BGs (46 μg RV/$1\times10^{10}$ BGs) are depicted (B). Whereas 15 μM RV did not differ from the control, 30 μM RV resulted in 20% loss of viability. Stimulatory growth of macrophages was observed after treatment with RV-BGs in a MOI of 10 and 100. Coincubation in a ghost to cell ratio of 1000 led to significant decrease in cell viability (P=0.0462). Bars indicate mean values+SD. Each experimental point represents values form four independent cultures measured in triplicate. Asterisks indicate values which are significant different from their respective control (p<0.05). Analyses were performed with unpaired two tailed Student's t-test.

The invention is further illustrated by the following non-limiting examples.

EXAMPLES

Example 1

Bacterial Ghosts Promote Innate Immune Responses in Human Keratinocytes

Little is known about the capacity of BGs to induce the expression of innate immune modulators by epithelial cells especially human KCs. In the present study the ability of *E. coli* BGs to induce antimicrobial peptides and pro-inflammatory cytokines expression in human primary KCs has been investigated. Obtained results demonstrate that the presence of flagellin on the surface of BGs enhance the expression of the antimicrobial psoriasin and hBD-2, and the release of interleukin (IL)-6 and IL-8 by human KCs.

Materials & Methods

Cell Culture

Human primary KCs prepared from neonatal foreskin were obtained from Clonetics (San Diego, Calif., USA) and cultured in serum-free keratinocyte growth medium (KGM, Clonetics) as described previously (Rendl et al., 2002. J. Invest Dermatol. 119:1150-1155). For stimulation, third passage KCs were cultured in 12-well tissue culture plates (Corning Incorporated, Corning, N.Y., USA) and used at a confluence of 60-70%. Stimulation was performed in keratinocyte basal medium (KBM, Clonetics).

RNA Isolation and qRT-PCR

After stimulation, cells were washed with phosphate-buffered saline (PBS) and RNA was isolated using TRIzol® Reagent (Invitrogen, Carlsbad, Calif., USA) according to the manufacturer's instructions. For cDNA synthesis RNA was reverse-transcribed with MuLV-reverse transcriptase using the Gene Amp RNA PCR kit (Applied Biosystems, Foster City, Calif., USA) and oligo dT primers (Roche Diagnostics, Basel, Switzerland). cDNA sequences of the genes under investigation were obtained from the GenBank. Primers were designed using the PRIMER3 software from the Whitehead Institute for Biomedical Research (Cambridge, Mass., USA). The following forward (F) and reverse (R) intron-spanning primers were used for β-2-microglobulin (B2M): F, 5'-GATGAGTATGCCTGC-CGTGTG-3';

R, 5'-CAATCCAAATGCGGCATCT-3';

psoriasin: F, 5'-GGAGAACTTCCCCAACTTCCTT-3;

R, 5'-GGAGAAGACATTTTATTGTTCCT-3'-qRT-PCR was performed by the LightCycler technology using the Fast Start SYBR Green I kit for amplification and detection (Roche Diagnostics). In all assays, cDNA was amplified using a standardized program (10 min denaturing step and 55 cycles of 5 sec at 95° C.; 15 sec at 65° C., and 15 sec at 72° C.; melting point analysis in 0.1° C. steps; final cooling step). Each LightCycler capillary was loaded with 1.5 µl DNA master mix; 1.8 µl MgCl$_2$ (25 mM); 10.2 µl H$_2$O; and 0.5 µl of each primer (10 µM). Determination of the relative quantification of target gene expression and amplification efficiencies were performed using a mathematical model by Pfaffl (Pfaffl. 2001. Nucleic Acids Res. 29:e45). The expression of the target gene was normalized to the expression of the housekeeping gene β-2-microglobulin. All real-time PCRs were performed in triplicate. The specificity of PCR reactions was confirmed by sequencing of the PCR products.

BGs Production and KCs Stimulation

*E. coli* NK9373 (wt) and *E. coli* NK9375 (ΔfliC), a flagellin-deficient strain having an in frame deletion within the fliC gene (Bates et al., 2005. Mol. Microbiol. 57:380-391) were kindly provided by Dr. David Bates (Baylor College of Medicine, Houston, Tex.). *E. coli* strains harbouring the lysis plasmid pGLysivb (unpublished) were grown in animal free Lennox Broth (LBv; 10 g/l sojapeptone, 5 g/l yeast extract, 5 g/l NaCl) containing gentamycin (20 µg/ml) at 35° C. Two liter of medium were inoculated with 4 ml glycerine stock, descending from one single transformant colony and used as a preculture for fermentation after over night incubation. Fermentations were performed in 20 l medium using a Techfors S fermenter (Infors Ag, Bottmingen, Switzerland). Following parameters were documented: temperature, flow, stirrer, pH, pO$_2$, foaming and pumps for acid, base and antifoam. Growth and lysis of the bacteria were followed by measuring the optical density (OD$_{600}$), by determination of the colony forming units using a spiral plater (WASP system, Don Whitley Scientific Limited, West Yorkshire, UK) and by microscopy of periodically taken samples. Bacteria were grown in LBv medium set to pH 7.2 with aeration and agitation (flow and stirring controlled by a programmed sequence) to mid-logarithmic stage. Expression of the lysis protein E was induced by temperature upshift to 42° C. After the completed lysis process (reaching a plateau in the pO$_2$ level) the remaining intact bacteria were killed by addition of beta-propiolacton (BPL). A total of 0.075% BPL was added in two equal doses with a time gap of 30 min. For incubation with BPL the stirring rate was set to 600 rpm. For harvesting by a seperator (CTC1, GEA Westfalia Separator GmbH, Oelde, Germany) the temperature was set to 16° C. and a flow rate of about 200 ml/min was used. The system was rinsed with 5 l sterile, distilled water before resuspension of the BG pellet and BGs were subsequently washed by 5 resuspension/centrifugation cycles with distilled water in a total volume of 7.5 l using a Hermle ZK 401 centrifuge (Hermle Labortechnik GmbH, Wehingen, Germany) at 8,000 min$^{-1}$, 4° C., 15 min. The final pellet was resuspended in 200 ml distilled water, aliquoted into lyophilisation bottles and stored at –80° C. Samples were lyophilized for about 60 h using a Lyolab B (LSL Secfroid, Aclens, Switzerland) lyophilisator.

Lyophilized BGs from *E. coli* NM522, *E. coli* NK9373 (wt) and *E. coli* NK9375 (ΔfliC) were resuspended in KBM medium before applying on KCs. For in vitro assays recombinant IL-1α (R&D Systems, Minneapolis, Minn., USA) and purified flagellin from *S. typhimurium* (Invitrogen) were used. Culture supernatants of wt and ΔFliC *E. coli* were prepared as described in Abtin et al. (FASTEB J 22 (2008), 2168-2176). Before KCs stimulation culture supernatants were diluted 1:100 in KBM.

Cytokine Measurement

Culture supernatants of stimulated KCs were depleted of detached cells or cell fragments by centrifugation and stored at –20° C. until analysis. Concentrations of IL-6 and IL-8 were determined by enzyme-linked immunosorbant assay (ELISA; R&D Systems) according to the manufacturer's instructions.

Immunoblot Analysis

For analysis of protein expression, KCs were lyzed in SDS-PAGE loading buffer (50 mM Tris, pH 7.4, 2% SDS). After sonication insoluble cell debris was removed by centrifugation and protein concentration was measured by the BCA (bicinchoninic acid) method (Pierce, Rockford, Ill., USA). Western blot analysis was performed as described previously (Mildner et al., 2006. Biochem. Biophys. Res. Commun. 348:76-82). Equal loading of protein lysates was confirmed by Ponceau S staining of the membrane. The following first step antibody was used: mouse monoclonal IgG, anti-psoriasin clone 47C1068 (dilution 1:500; Abcam, Cambridge, UK). The membranes were developed using the Chemiglow reagent (Alpha Innotech, San Leandro, Calif., USA) according to the manufacturer's instructions.

ImageJ software based analysis was applied to quantify the densities of bands obtained via immunoblot blot analysis (Rasband, W. S., ImageJ, U.S. NIH, Bethesda, Md., USA; http://rsb.info.nih.gov/ij/, 1997-2009). Obtained values of psoriasin expression after stimulation of KCs with various particle concentrations of wt and ΔFliC *E. coli* BGs were normalized to the value of psoriasin expression obtained after stimulation of KCs with recombinant IL-1α.

Fluorescein Isothiocyanate (FITC)-labeled BG Uptake

The efficiency of the endocytic activity of the human primary KCs was measured as described previously (Kudela et al., 2007. Cancer Lett. 1:54-63; Kudela et al., 2005. J. Immunother. 28:136-143). Briefly, human primary KCs cultured in 24 well plates ($2 \times 10^5$ cells/well) were incubated with FITC-BG (1000 per cell) for 2 hours at +37° C. After the incubation cells were washed three times with PBS to remove the excess BGs. Finally the cells were detached using TrypLE™ Express (Invitrogen), washed twice with PBS, fixed in cold 1.5% paraformaldehyde (Sigma-Aldrich, St. Louis, Mo.) in PBS and analyzed on BD FACSCanto™ Flow Cytometer (BD Biosciences, Pharmingen, San Jose, USA).

Statistical Analysis

Obtained results were analyzed by GraphPad Prism version 5 (GraphPad Software, La Jolla, Calif.). The statistical significance of the difference between two groups was evaluated by Student's t-test and between more than two groups by the one-way ANOVA. Differences were considered to be significant with $p<0.05$.

Results

Expression of Antimicrobial Peptides by BGs in Human Primary KCs

It has been reported that *E. coli* culture supernatants induce the expression of the antimicrobial peptides psoriasin and hBD-2 in epidermal KCs (Abtin et al., 2008. FASEB J. 7:2168-2176; Glaser et al., 2005. Nat. Immunol. 6:57-64). To investigate the capacity of BGs to elicit innate immune responses by epithelial cells, human primary KCs were stimulated for 24 hours with different particle concentrations of BGs generated from wt *E. coli*. Stimulation of KCs by flagellin (10 ng/ml) and IL-1α (10 ng/ml) served as positive control for the up-regulation of the analyzed antimicrobial peptide, untreated cells served as negative control. The relative mRNA up-regulation of the antimicrobial psoriasin was determined by quantitative real-time PCR (qRT-PCR). As can be depicted from FIG. 1 the mRNA expression of psoriasin was up-regulated in KCs after incubation with BGs. The stimulated psoriasin mRNA production was dependent on the BG particles and the strongest up-regulation was observed at $2 \times 10^8$ BG particles/ml, BG concentrations below $2 \times 10^8$ particles/ml had no effect (FIG. 1).

We have previously reported that the induction of psoriasin in KCs is dependent on flagellin expression by *E. coli* (Abtin et al., 2008. FASEB J. 7:2168-2176). To investigate whether flagellin of BGs has a similar effect, we generated BGs from the wild-type (wt) NK9373 and the isogenic flagellin-deficient (AMC) NK9375 *E. coli* strains. As positive controls KCs were stimulated with flagellin, IL-1α and culture supernatant from wt *E. coli*. KCs incubated in the presence of non-conditioned bacterial culture medium, culture supernatant from ΔFliC *E. coli*, and without stimulation served as negative controls. KCs were stimulated for 48 hours and afterwards analyzed by immunoblot for psoriasin protein production. In contrast to the mRNA data a faint band of psoriasin was detected on the protein level at $2 \times 10^7$ BG particles/ml (FIG. 2A). Strong induction of psoriasin was observed at $2 \times 10^8$ particles/ml which was even stronger at $2 \times 10^9$ particles/ml by wt (NK9373) *E. coli* BGs. For the isogenic ΔfliC (NK9375) strain a faint band of psoriasin was detected starting at $2 \times 10^8$ BG particles/ml with a prominent expression level at $2 \times 10^9$ BG particles/ml (FIGS. 2A, B).

Expression of Cytokines in Human Primary KCs After Treatment with BGs

The secretion of the pro-inflammatory cytokines IL-6 and IL-8 by KCs after incubation for 48 hours with BGs was investigated by ELISA. The release of IL-6 and IL-8 by KCs after the incubation with wt (NK9373) and ΔfliC (NK9375) *E. coli* BGs was dependent on the BG source and used particle numbers (FIGS. 3A, B). Obtained results showed that the effect of wt (NK9373) *E. coli* BGs on IL-6 and IL-8 release was detectable beginning at concentrations $2 \times 10^7$ particles/ml. While concentrations below $2 \times 10^7$ particles/ml were almost ineffective, $2 \times 10^9$ particles/ml strongly enhanced the secretion of IL-6 from 2 pg/ml (untreated) to 600 pg/ml and IL-8 from 60 pg/ml (untreated) to 1350 pg/ml, respectively (FIGS. 3A, B). However, ΔfliC (NK9375) *E. coli* BGs increased the secretion of both cytokines only when using $2 \times 10^9$ particles/mi to 134 pg/ml and 750 pg/ml of IL-6 and IL-8, respectively, whereas BGs concentrations below that had no significant effect on the release of both cytokines (FIGS. 3A, B). Furthermore, significant difference in secretion of both IL-6 and IL-8 related to the presence of flagellin was detected after incubation of KCs with culture supernatants from wt *E. coli* and ΔFliC *E. coli*, when cytokine production was nearly one order of magnitude lower after incubation of KCs in the presence of culture supernatant from ΔFliC *E. coli* compared to culture supernatant from wt *E. coli* (FIGS. 3A, B). Altogether these results emphasize the importance of intact envelope surface structure of BGs and the role of flagellin in the stimulation of innate immune system.

Endocytosis of wt (NK9373) and ΔfliC (NK9375) *E. Coli* BGs by Human Primary KCs As mentioned above, the up-regulation of antimicrobial psoriasin and enhanced release of pro-inflammatory cytokines by KCs is dependent on the presence of flagellin on the surface of BGs. To further investigate the role of flagellin in the uptake of BGs by KCs, endocytosis of wt (NK9373) and ΔFliC (NK9375) *E. coli* BGs were compared and analyzed. Missing flagellin on the surface of BGs caused significant decrease (~6-fold less) of KCs capacity to bind and endocyte BGs. FACs analysis clearly showed the difference between the internalization of FITC-labeled wt *E. coli* BGs (FIG. 4A) and to ΔFliC *E. coli* BGs (FIG. 4B). As depicted in FIG. 4C approximately 6 fold increase of KC's capacity to bind and internalize wt *E. coli* BGs compared to ΔFliC *E. coli* BGs was observed due to the presence of the intact flagellin.

Discussion

BGs are non-living cell envelope preparations from Gram-negative bacteria, devoid of cytoplasmic contents, while their cellular morphology and native surface antigenic structures remain preserved [40]. In this investigation the effects of BGs on the regulation of innate immune modulators using human primary KCs were determined. Incubation of BGs generated from non-pathogenic *E. coli* with human KCs up-regulated the expression of the antimicrobial psoriasin. This was in agreement with earlier reports where culture supernatants or disrupted cells of *E. coli* strains enhanced the expression of antimicrobial peptides [2]. Therefore, this investigation confirmed that the envelope structures of BGs including flagellin are fully functional and intact, and are recognized by KCs promoting the innate immune responses similar to bacterial compounds used in the former studies [2].

As reported earlier, the responsiveness towards *E. coli* by KCs is mediated through TLR5 and its ligand flagellin [2]. The wt *E. coli* exhibited a BG concentration-dependent induction of psoriasin production (FIG. 1); whereas the ΔFliC *E. coli* showed the expression of psoriasin at BG concentrations of one order of magnitude higher than the wt strain (FIG. 2). Accordingly, the data obtained from the release of the pro-inflammatory cytokines IL-6 and IL-8 underlined the significance of the presence of flagellin in the BGs preparation when compared to the ΔFliC mutant strain (FIG. 3). From the previous studies with supernatants of *E. coli* as source of shad flagellin and/or purified flagellin, it is evident that flagellin is the major inducer of psoriasin in human KCs [2]. However, since ΔFliC BGs are capable of psoriasin induction there seems to be additional FliC-independent pathways.

Furthermore, investigation of BGs uptake by KCs derived from wt *E. coli* and ΔFliC *E. coli* showed that the BGs from the flagella bearing strain is taken up roughly one order of magnitude better than the ΔFliC BGs (FIG. 4). This observation suggests that the presence of flagellin on the BG surface contributes to the binding and internalization of BGs by KCs. Moreover, the key role of flagellin in the induction of psoriasin production, and IL-6 and IL-8 secretion is reflected by decreased response of KCs in production of these proteins after incubation with ΔFliC *E. coli* BGs or incubation with culture supernatant from ΔFliC *E. coli*. The question remains whether other components on the surface e.g. LPS of the ΔFliC *E. coli* BGs have signaling activities for the production of antimicrobial peptides and/or pro-inflammatory cytokines. The release of IL-6 and IL-8 by KCs, however, were more sensitive to the presence of flagellin as no direct correlation with the BGs particle number could be detected (FIG. 3). Higher secretion of IL-8 compared to IL-6 by KCs after incubation with AFliC BGs (FIG. 3) and partial internalization of BGs from ΔFliC *E. coli* (FIG. 4) might be related to the presence of the LPS on the BG's shell. Presence of LPS from disrupted bacterial cells presented in the culture supernatant could explain detected low secretion of IL-8 by KCs after incubation with culture supernatant from ΔFliC *E. coli* (FIG. 3B). It was shown previously that activation of skin melanoma cells by LPS results in enhanced production of IL-8 and cell adhesion (Malteni at al., Cancer Lett. 235 (2006), 75-83). Although it has been reported that TLR4 is not involved in cellular LPS uptake by endothelial cells, the connection between TLR4-mediated epidermal KCs activation by LPS and their phagocytic activity remains to be defined (Dunzendorfer et al., J. Immunol. 173 (2004), 1166-1170). Despite the fact that functional expression of TLR4 on the surface of KCs was observed by some investigators but not by other investigations [2], intact LPS on the BG's envelope might contribute to the complex process during recognition of bacterial components by human skin cells including KCs. Therefore, the exact role and the mechanisms involved during activation of epidermal KCs through LPS signaling have to be determined.

It is still possible that the acidic degradation of the flagella present in wt *E. coli* BGs in the lysosomal compartment of KCs leads to monomeric flagellin, which is able to bind to TLR5 and stimulate the expression of the cytokines IL-6 and IL-8 and the production of psoriasin. As flagellin binding to TLR5 [2] cannot occur with the ΔFliC BGs and consequently the signalling induced by this binding, other ways of internal signalling leading to NF-kappaB induced expression of psoriasin have to be induced by BGs in KCs. Possible intracellular receptors which might sense the presence of BGs or BGs constituents irrespective of flagellin expression are the NLRs such as NOD1 or NOD2. Recent investigations have reported the functional expression of NOD1 [22] and NOD2 [2] by peptidoglycan fragments in KCs. In particular, NOD1 mediates the sensing of peptidoglycan fragments containing the amino-acid meso-diaminopimelic acid and NOD2 mediates the sensing of muramyl dipeptide [2], which both of these fragments are degradation products of the still intact peptidoglycan of *E. coli* BGs [60]. The connection between activation of NOD2 by muramyl dipeptide (MDP) and increased antimicrobial peptides production in primary KCs has been reported [2], and in our study the use of BGs to induce psoriasin has been demonstrated. Therefore, obtained results demonstrate the ideal use of non-living and safe BGs in therapeutic approaches to enhance the innate immune defence system of the skin. Potential therapeutic effects of BGs can be combined by packaging drugs or other biological active substances into BGs which could also be delivered intracellular for the stimulation of additional beneficial health effects [2].

Example 2

Modulating Action of NO Production in RAW 264.7 by Resveratrol Loaded Bacterial Ghosts As demonstrated in earlier studies, BGs have quite an impact on the parameters of the innate immune system like the secretion of cytokines and expression of antimicrobial peptides. Taken into consideration that iNOS-induced production of NO, a keyplayer molecule in innate immunity, is stimulated by LPS we examined the extent of BG-stimulated radical release. Moreover, the impact of RV-loaded ghosts was investigated in regard to modulated chemicals-caused anti-inflammatory (decrease of NO-production) as well as anti-proliferation activity.

Materials & Methods

Chemicals

If not otherwise stated, all chemicals were obtained from Sigma Aldrich.

Cell Culture

RAW 264.7 cells obtained from the American Type Culture Collection (ATCC, USA), were cultured in Dulbecco's Modified Essential Medium with 4.5 g/L glucose (DMEM; Lonza BioWhittaker; W/O Glut P-red) supplemented with 2 mM L-Glutamine (Lonza Bio Whittaker) and with 10% heat-inactivated fetal calf serum (Gibco; Invitrogen). Additionally, 100 U Pen-Strep (Lonza) were added to the cultivation medium. For assessment of the viability, another medium was used. There, the cells were cultured in Roswell Park Memorial Institute Medium (RPMI) 1640 supplemented with 10% heat inactivated fetal calf serum (FCS), penicillin (104 µg/ml), streptomycin (100 µg/ml), 200 mM L-glutamine, HEPES buffer (10 mM), 10% non essential amino acids (NEAA) and plasmocin (5 µg/ml, Lonza).

The cells were cultured 45-48 h (37° C.; 5% $CO_2$) until they reached their confluent state. Media which were used for analyses of the various experiments contained only antibiotics.

Bacterial Ghost Production

BGs from *E. coli* NM522 (pGLysivb; 240106-5/6), were produced by the controlled expression of the phage-derived lysis protein E as described elsewhere (Witte et al., 1992. Arch Microbiol. 157(4): p. 381-8; Mayr et al., 2005. Infect Immun 73(8): p. 4810-7). Inactivation of the non-lysed bacteria was done by addition of antibiotics. Lyophilized BGs were stored at room temperature (1 mg lyophilized weight contained $1.27*10^{10}$ particles). BGs were resuspended in test-medium prior to treatment experiments.

Loading BGs with Resveratrol

A 12-24 mg amount of lyophilized BGs was suspended in different resveratrol concentrations (1-35 mg RV/ml methanol) and incubated with vigorous shaking (800 rpm) for 30 min at 28° C. The loaded BGs were collected by centrifugation at 13000 rpm for 15 min and the pellets were washed three times with water. 1 mg BG aliquots were stored at −20° C. until use.

Nitrite Assay

RAW 264.7 cells were seeded in 96 well plates and were cultured for two days. Approximately $3*10^5$ macrophages per well were then stimulated either with 200 µl defined concentrations of empty BGs (positive control) or with resveratrol-loaded ghosts (46 µg RV/1×$10^{10}$ BGs), or with empty bacterial ghosts plus defined resveratrol concentrations given externally, for 20 min. Thereafter, the bacterial ghost suspensions were removed by twice washing with PBS and the cells were incubated for another 20 hours in the dark at 37° C. 5% $CO_2$. In order to investigate the stimulatory impact of pure LPS (Fluka; E. coli serotype 055:B5), long-term incubation experiments with various LPS concentrations were conducted for 20 hours.

As an indicater of NO production, nitrite concentration was measured in the supernatant of the macrophages by use of the Griess reaction (Green et al., 1982 Anal Biochem. 126(1): p. 131-8). In short, 100 μl of each supernatant was mixed with 90 μl 1% sulphanilamide (Fluka) in 5% $H_3PO_4$ and 90 μl of N-(1-Naphthyl) ethylene diamine dihydrochloride in water. The absorbance was determined at 550 nm with an ELISA reader (Tecan Sunrise).

Uptake Studies

Application and detection of FITC-labeled BGs to RAW 264.7 As an indication for endocytic resveratrol delivery, uptake of FITC-labeled BGs was determined in the analyzed cell line. For this purpose, lyophilized bacterial ghosts (5-15 mg were resuspended in 1.5 ml 0.1M $Na_2CO_3$; pH ~9.0. Thereafter, 25 μl of FITC stock solution (2 mg FITC in 1 ml DMSO) was added to the BG suspension and shaken for 2 h in the dark at 16° C. After five washing steps with PBS (5 min; 14000 rpm) and check for positive labeling, the ghostpellets were resuspended again in sodium carbonate buffer and stored at −20° C. until use.

Culturing and treatment of RAW 264.7 was the same as for the nitrite assay but with minor modifications. After 20 min incubation with defined amounts of empty BGs the macrophages were washed twice with PBS and the washing solutions were collected in empty neighbouring wells. Fluorescence was then recorded with a Tecan Geniospro fluorometer at excitation and emission wavelengths 485/535 (gain 40). Total fluorescence values were taken as 100% of the applied ghost amount and uptake was calculated from the resulting fluorescence per macrophage.

Cytotoxicity Assays

The neutral red assay was used to test the impact of empty or RV-loaded BGs as well as the chemical per se on the viability of RAW 264.7 cells. Neutral red (3-amino-m-dimethylamino-2methyl-phenazine hydrochloride) selectively accumulates in lysosomes of living cells (Repetto et al. 2008. Nat Protoc, 2008. 3(7): p. 1125-31) and provides therefore a quantitative assessment of viablitity.

Individual wells of 96-well plates were inoculated with $1.25 \times 10^5$ cells and were allowed to attach overnight. Macrophages were treated with 200 μl medium containing RV-loaded and unloaded BGs (all resuspended in sf-medium) in different BG to cell ratios (10, 100, 1000) or with RV alone for either 20 min followed by a 20 hour recovery period or 24 hours. The same conditions were performed with two RV-concentrations (15 μM and 30 μM). Triton X-100 (0.01%) served as a positive control and cells treated with test medium represent the negative control. After treatment, the cells were washed twice with PBS and were incubated either with culture medium for 20 hours or directly with 100 μl of NR (80 μg/ml final concentration) for another two hours (37° C.; 5% $CO_2$). Thereafter, the dye was discarded and the wells were washed two times with PBS. Extraction of the dye was accomplished by addition of 100 μl of the acidic destaining solution (1 ml acetic acid, 73 ml 96% ethanol and 26 ml deionized water). The plates were shaken for 10 min and the developed color was measured by a plate reader (Dynex OpsysMR) at 570 nm (reference wavelength 690 nm).

Statistics

All results were analysed by use of GraphPad Prism (version 5, GraphPad Software, Inc; San Diego; Calif., USA). Data are expressed as means+SD. Statistical analysis was performed by the use of Student's t-test. P-values <0.05 were considered statistically significant.

Results

Loading of BGs with RV

The loading of lyophilized E. coli NM522 BGs with RV was performed by simple resuspension of BGs within the desired RV-solution. To determine the amount of RV in BGs, ethanolic extractions were performed and analyzed via HPLC. The results are depicted in FIG. 5A. A clear dependency between the loading concentration of RV and recovered RV could be observed (correlation coefficient $r^2=0.9980$). The highest loading efficiency was obtained after suspension of lyophilized BGs in a 35 mg/ml RV solution. On average 46 μg RV could be detected after extraction of $1 \times 10^{10}$ BGs. Approximately 4% of the stock solutions were recovered when the amount of lyophilized ghosts at the beginning was considered.

Adherence and Uptake of FITC-Labeled BGs by Murine Macrophages

Fluorometric quantification experiments were conducted in order to investigate the amount of BGs which are either cell associated or uptaken by murine macrophages after short time of coincubation. FIG. 5B depicts the results obtained by fluorometric measurements of RAW 264.7 and E. coli NM522 BGs after 20 min coincubation and two washing steps. A clear dose dependency of applied and cell-associated ghosts can be seen, leading to a nearly perfect linear regression (correlation coefficient $r^2=0.998$). Furthermore, no differences where observed when the experiments were performed in 96 or 24 well plates (data not shown). On average 25% of the applied ghosts were associated with macrophages after this short incubation time.

To clarify if BGs are also already taken up by murine macrophages within this period, confocal laser scanning microscopy (CLSM) studies were conducted in which the internalization was visually examined. For this purpose, z-stacks were performed after incubation of FITC-labeled E. coli NM522 ghosts with RAW 264.7 cells after 20 and 40 minutes. Macrophages were stained with Texas-Red phalloidin, which selectively binds to F-actin skeleton of the cells. Images displaying representative single z-stacks of various opticals sections are depicted in FIG. 6A and FIG. 6B. It can be seen that FITC-labeled BGs which are already internalized by the cells that are stained in red, appear yellow. Green colored BGs represent those which are not engulfed and are attached outside to the cell. Furthermore, at a BG-to cell ratio of 1000, we observed ingested BGs as well as clusters of internalized BGs in every macrophage.

Induction of NO Production

Because iNOS is induced by LPS, the NO production was investigated after stimulation of RAW 264.7 cells with different concentrations of LPS for 20 hrs. As depicted in FIG. 7A, treatment with 1-1000 ng/ml LPS led to the generation of NO with a significant sensitivity starting at 1 ng/ml. Due to the fact that BGs fully maintain their LPS molecules bound in the envelope, experiments were conducted to determine to which extent BGs are able to stimulate NO production. It turned out that a ghost to cell ratio of 10 was already enough to significantly induce NO generation (P=0.0005), of a level similar to 1 ng/ml of free LPS.

Clear particle-dependent stimulation of NO generation was achieved when cells were treated with empty BGs with a MOI of 100-1000. However, higher concentrations of BGs (2000 and 5000 particles per cell) did not show any further impact.

Modulating Capacity of NO-Stimulation by BG Themselves and RV-Loaded BGs in Contrast to Externally Given RV As already shown in FIG. 7B BGs are able to stimulate NO production in a dose dependent manner when they are applied to macrophages in a BG to cell ratio between 100 and 1000.

Since many studies showed that RV is capable to reduce LPS-induced NO-production (Saiko et al., 2008. Mutat Res. 658(1-2): p. 68-94; Tsai et al., 1999 Br J Pharmacol. 126(3): p. 673-80), experiments were conducted to investigate the potential of RV to modulate the BGs induced NO-production. For this purpose empty *E. coli* NM522 BGs were applied to the cells in a ratio of 500. Coevally, three different concentrations of RV were added to the cell cultures. After 20 min coincubation and two washing steps, the production of NO was measured after 20 hours. The results are depicted in FIG. 8A. It can be seen that simultaneous treatment of empty *E. coli* NM522 ghosts together with 0.3 μM and 0.3 μM RV had no impact on BG-induced NO-generation. Statistically significant difference was observable after treatment with 30 μM RV ($P=0.0078$).

Based on the entrapped amount of RV in BGs (FIG. 5A) and the number BGs which were associated with macrophages (adhered to and taken up by the cells) after 20 min treatment (FIG. 5B), the BG-delivered resveratrol particles could be determined. As stimulation of NO-induction in RAW 264.7 cells was performed with BGs having the highest RV-yield (46 μg RV/$1\times10^{10}$ BGs) in a MOI of 100 and 1000, calculated RV-delivery values by BGs would correspond to $0.48+0.25$ μM and $8.86+2.21$ μM resveratrol ($5.8\times10^{13}$ and $1.07\times10^{15}$ RV-particles per 200 μl).

In order to investigate if RV bound in BGs may have a modulating mode on the NO production, the impact of the same amount of empty ghosts versus RV-loaded ghosts was analysed. Additionally, the radical release due to simultaneously application of empty BGs and 3 μM RV ($3.61\times1014$ RV particles/200 μl) was assessed.

It can be seen that externally applied RV together with empty *E. coli* NM522 BGs did not decrease the radical release as effective as compared to RV-loaded ghosts. Our findings show that a significant reduction of nitrite was found with RV-loaded ghosts in a BG to cell ratio of 100 ($P=0.0048$) whereas 3 μM RV had no effect (FIG. 8B). On the other side, results obtained after treatment of macrophages in a MOI of 1000 led to reduction with both variants. Nevertheless, significant lower amounts of NO were produced when RV-ghosts were applied to RAW 264.7 cells than with 3 μM RV administered coevally with empty BGs ($P=0.0002$ vs. $P=0.0158$) compared to treatment with BGs alone (FIG. 8C).

Determination of Cell Viability

In order to investigate the impact of empty and RV-loaded BGs (46 μg RV/$1\times10^{10}$ BGs) on the cell viability of RAW 264.7 macrophages two different treatment conditions were examined with three different BG to cell ratios (10, 100, 1000). The first test was performed the same way as described for NO-measurements, i.e. 20 min treatment followed by measurement after 20 hours. The second analysis concerned the effects of long-term incubations for 24 hours. As depicted in FIG. 9A, *E. coli* NM522 ghosts per se had no cytotoxic impact within this period. Nevertheless, 24 hours incubation of macrophages with BGs in an MOI of 10 led to a significant growth stimulatory effect ($P=0.0016$), whereas higher BG-concentrations did not differ from the serum-free medium treated controls. While no effects were seen after short-term coincubations with RV-loaded ghosts nor with the chemical per se (data not shown), enhanced metabolic activity was found after treatment with RV-BGs in an MO of 10 and 100 ($P=0.0008$ and $0.0111$) after 24 hours (FIG. 9B).

As we did not determine the cell-associated amount of BGs after 24 hours incubation, no adequate statements can be made for the delivered RV concentration by BGs.

Theoretically, if all applied BGs in a MOI of 1000 would be taken up by the macrophages, the level of 30 μM would be reached. However, we know from microscopic investigations that this can not be true. Assuming, that half of the BG amount will be engulfed in this period, a calculated concentration of 15 μM resveratrol would be obtained. Therefore, comparative experiments were conducted in which the impact of 15 μM and 30 μM RV on the cell viability was investigated in contrast to RV bound in BGs (46 pg RV/$1\times10^{10}$ BGs) which were applied in a ghost to cell ratio of 1000. Whereas, the lowest chemical concentration had no impact at all, the cell viability was drastically decreased after treatment with 30 μM RV ($81.23+10.6\%$). Significant decrease in cell viability was also observed with RV-BGs ($P=0.0462$). On average, 10% of the cells died due to the delivered chemical (FIG. 9B).

Discussion

In the present study we have demonstrated that BGs are inducing NO-formation by macrophages and that this activity can be modulated by RV-loaded BGs.

The dependency on the activity of iNOS and NO-release to cure pathogen-caused diseases, e.g. Leishmaniasis or Tuberculosis, has been demonstrated in several studies (Bogdan, C., 2000 Immunol Rev. 173: p. 17-26; Sharma et al., 2007. Inflammopharmacology 15(6): p. 252-9; Chakravortty and Hensel, 2003. Microbes Infect. 5(7): p. 621-7). It is known in general, that pathogens are phagocytosed by cells of the innate immune system. Results from other studies, demonstrate that BGs are preferentially engulfed by those cells and uptake has been reported for various macrophage cell lines and dentritic cells (Haslberger et al., 2000. J Biotechnol. 83(1-2): p. 57-66; Kudela et al., 2005. J Immunother. 28(2): p. 136-43; Paukner et al., 2003 J Drug Target 11(3): p. 151-61). In accordance with earlier findings, uptake could be confirmed in the RAW 264.7 macrophage cell line after short-term coincubation of BGs. Interestingly, microscopic observations with CLSM showed that macrophages are capable to engulf single as well as cluster of ghosts.

As BGs possess all their pathogen-associated molecular patterns (PAMPs) like their natural counterpart, they are recognized by their corresponding host innate immune receptors, e.g. Toll-like receptors (TLRs). Therefore, bacterial LPS interacts with TLR4 and flagellin with TLR5 (Ishii et al., 2008 Cell Host Microbe. 3(6): p. 352-63). Uptake of BGs in the murine RAW 264.7 macrophage cell line is mainly related to TLR4 as they hardly express TLR5 (Applequist et al., 2003. Int Immunol. 14(9): p. 1065-74). On the other hand, in Example 1, it is shown that *E. coli* BGs enter primary keratinocytes by the flagellin-dependent TLR5 pathway as well as other uptake mechanisms. Investigations from Panaro et al. with human macrophages demonstrate a direct correlation between LPS-induced NO-generation. The efficacy was significantly reduced in both parameters, when L-NMMA, a competitive inhibitor of i-NOS, was present (Panaro et al., 1999. Int J Clin Lab Res. 29(3): p. 122-7).

Because LPS is renowned for the induction of iNOS through interaction with TLR-4 (Bogdan, C., 2001. Nat Immunol 2(10): p. 907-16), we conducted comparative experiments between long-term incubation (20 hrs) with free LPS and short-term incubation with various amounts of BG (20 min followed by determination of NO-release after 20 hours) in RAW 264.7 cells. It turned out that treatment of macrophages with *E. coli* ghosts in a MOI of 10 showed the same effect than 100 ng/ml LPS, which was found to be accountable for parasite elimination by Panaro et al. (Panaro et al., 1999. Int J Clin Lab Res. 29(3): p. 122-7). Furthermore, we analysed the relation between the observed particle-dependent BG-cell association with the extent of NO-release and found a significant positive correlation (Spearman r=1; P value=0.0167).

Besides NO-generation, other factors like cytokines trigger the innate immune response towards intracellular pathogens. Type I interferons such as IFNγ are produced by a variety of cells and exert potent antimicrobial activities. In earlier studies it was demonstrated, that BGs possess the feature to stimulate cytokine productions. For example, Ebensen et al. demonstrated that application of *M. haemolytica* BGs led to an increment of the amount of splenic IFN-γ-producing cells in immunized mice (Ebensen et al., 2004. J Immunol. 172(11): p. 6858-65). In another animal study the splenic IFNγ level was significantly increased after immunization with *E. coli* 0157:H7 BGs (Mayr et al., 2005. Infect Immun 73(8): p. 4810-7). As it is known that IL-12 enhances IFNγ production and plays a pivotal role in the development of Th1 cells investigations with BGs were performed and effective stimulation of IL-12 production in antigen presenting cells was reported by Haslberger et al. (Haslberger et al., 2000. J Biotechnol. 83(1-2): p. 57-66).

Coming back to NO-production, results from investigations with resveratrol demonstrated its suppressing character towards iNOS induction (Saiko et al., 2008. Mutat Res. 658 (1-2): p. 68-94; Tsai et al., 1999 Br J Pharmacol. 126(3): p. 673-80). Therefore, in the present study the effects of resveratrol, either coincubated with empty BGs or intracellular bound in BGs, towards BG-induced NO-production by RAW 264.7 macrophages were determined. Highly significant decrease in radical release was obtained by application of RV bound in BGs than compared with their empty version. Moreover, the externally added pure compound at a concentration level of 3 μM, which is roughly 6 times higher than the concentration delivered by the cell-associated ghosts in a MOI of 100, had no impact on NO-generation in comparison to the BG loaded application which reduced radical release for about 15%.

To our knowledge, the cellular uptake mechanism of resveratrol is still unclear. Till now, no specific receptor has been found for the drug. Due to its structure, resveratrol is able to interact with cell surface receptors like estrogen receptors or integrins (Saiko et al., 2008. Mutat Res. 658(1-2): p. 68-94; Lin et al., 2006 Faseb J. 20(10): p. 1742-4). However, due to our findings and the fact that intracellular delivery of resveratrol by RV-loaded BGs after uptake by macrophages, the existence of an internal resveratrol receptor is highly likely. We propose the term BGRV for such a hypothetical receptor.

It is known that bacterial LPS is responsible for manifold pathophysiological effects on a wide variety of mammalian cells. In the worst-case, endotoxic shock and multiple organ failure followed by death could be the consequence. This endotoxicity is mediated through the activation of the host immune and inflammatory cells, especially mononuclear phagocytes, which produce numerous bioactive mediators, including tumor necrosis factor alpha (TNF-alpha), interleukin 1, IL-6 and nitric oxide (Hirohashi and Morrison, 1996. Infect Immun. 64(3): p. 1011-5).

As the endotoxin content of Gram-negative bacteria is also present in BGs, saftety and toxicity studies with BGs have been performed in the last decade. Experiments were conducted in which preparations of bacterial ghosts derived from pathogenic *Escherichia coli* 026:B6 and *Salmonella typhimurium* C5 were investigated for their endotoxic activity by the use of standard Limulus amoebocyte lysate (LAL) assay and 2-keto-3-deoxyoctonate (KDO) assay (Haslberger et al., 2000. J Biotechnol. 83(1-2): p. 57-66; Mader et al., 1997. Vaccine. 15(2): p. 195-202). On average, both ghost species exhibited only 2-5% of the endotoxic activity compared to free LPS of *S. abortus* equi. Cell culture experiments with RAW 264.7 cells revealed 100-fold more BGs were required for the secretion of tumor necrosis factor alpha (TNFα) and prostaglandin E2 (PGE2) synthesis than compared to free LPS. The authors also highlighted that no significant fewer responses have been recorded in rabbits when BGs were administered i.v. at doses of <250 ng kg-1 which was sufficient for the induction of measurable immune responses in rabbits (Mader et al., 1997. Vaccine. 15(2): p. 195-202.).

Cytotoxic investigations were also performed in the present study. No killing effects of *E. coli* BGs per se were observed even when incubation was performed up to 24 hours. Thus, it is clearly shown that BG-related continuous stimuli for iNOS expression and production of high amounts of NO, does not cause cell death in vitro.

However, growth stimulatory effects were observed when cells were incubated with a low BG MOI of 10. Under the same treatment conditions this positive impact was even more enhanced when RV was loaded inside the particles. Nevertheless, a cytotoxic effect caused by BG-delivered RV could be further demonstrated after an application rate of 1000 BGs per cell for 24 hours. Resulting in approximately 10% decrease of cell viability it indicates another evidence for the effective RV-delivery by BGs. Besides anti-inflammatory effects, i.e. iNOS suppression, RV has been shown to cause anti-microbial (Chan, 2002. Biochem Pharmacol. 63(2): p. 99-104; Faith et al., 2006. Antiviral Res. 72(3): p. 242-51; Schriever et al., 2003 Atherosclerosis. 171(2): p. 379-80; Kedzierski et al., 2007. Parasitol Res. 102(1): p. 91-7) activity in vitro and its cancer chemotherapeutic potency has been found in various studies (for a review see Saiko et al., 2008. Mutat Res. 658(1-2): p. 68-94)

A short overview about the resveratrol contents in dietary sources is given by Udenigwe et al. The highest concentrations are found in red wines ranging from 2.3-46.3 μM (Udenigwe et al., 2008. Nutr Rev. 66(8): p. 445-54). Those values are comparable to the RV-content which was bound in BGs and delivered to the macrophages in the present study. However, those mentioned concentrations would require the consumption of one liter of the beverage. Furthermore, RV is known to be rapidly metabolized in the gut and liver within 8-14 min in vivo (Saiko et al., 2008. Mutat Res. 658(1-2): p. 68-94). As effects were observable with RV-BGs already after short coincubation with RAW 264.7 cells for 20 min, we suppose, that this metabolism maybe can be circumvented by protection of the substance due to the ghost's envelope and delayed cell specific delivery may be triggered in vivo.

As demonstrated in this study, BGs have a highly significant impact on stimulation of NO-generation in macrophages in vitro which was shown to be modifiable when RV bound to the interior of the BGs. Considering that NO-release as well as RV contributes to antimicrobial as well as anticancer effects and the fact that BGs enhance cellular cytokine secretion and antimicrobial peptides, highlights this system for use in therapeutic treatment of intracellular pathogens or cancer.

REFERENCES

1. Abtin, A., et al., Bacterial ghosts promote innate immune responses in human keratinocytes.
2. Abtin, A., L. Eckhart, M. Mildner, F. Gruber, J. M. Schroder, and E. Tschachler. 2008. Flagellin is the principal inducer of the antimicrobial peptide S100A7c (psoriasin) in human epidermal keratinocytes exposed to *Escherichia coli*. FASEB J. 7:2168-2176
3. Aggarwal, B. B., et al., Role of resveratrol in prevention and therapy of cancer: preclinical and clinical studies. Anticancer Res, 2004. 24(5A): p. 2783-840.
4. Akira, S. and K. Takeda. 2004. Toll-like receptor signalling. Nat. Rev. Immunol. 4:499-511.
5. Akira, S., S. Uematsu, and O. Takeuchi. 2006. Pathogen recognition and innate immunity. Cell 124:783-801.
6. Applequist, S. E., R. P. Wallin, and H. G. Ljunggren, Variable expression of Toll-like receptor in murine innate and adaptive immune cell lines. Int Immunol, 2002. 14(9): p. 1065-74.
7. Bates, D., J. Epstein, E. Boye, K. Fahrner, H. Berg, and N. Kleckner. 2005. The *Escherichia coli* baby cell column: a novel cell synchronization method provides new insight into the bacterial cell cycle. Mol. Microbiol. 57:380-391.
8. Bogdan, C., M. Rollinghoff, and A. Diefenbach, Reactive oxygen and reactive nitrogen intermediates in innate and specific immunity. Curr Opin Immunol, 2000. 12(1): p. 64-76.
9. Bogdan, C., M. Rollinghoff, and A. Diefenbach, The role of nitric oxide in innate immunity. Immunol Rev, 2000. 173: p. 17-26.
10. Bogdan, C., Nitric oxide and the immune response. Nat Immunol, 2001. 2(10): p. 907-16.
11. Chakravortty, D. and M. Hensel, Inducible nitric oxide synthase and control of intracellular bacterial pathogens. Microbes Infect, 2003. 5(7): p. 621-7.
12. Chan, M. M., Antimicrobial effect of resveratrol on dermatophytes and bacterial pathogens of the skin. Biochem Pharmacol, 2002. 63(2): p. 99-104.
13. Creagh, E. M. and L. A. O'Neill. 2006. TLRs, NLRs and RLRs: a trinity of pathogen sensors that co-operate in innate immunity. Trends Immunol. 27:352-357.
14. Dziarski, R. and D. Gupta. 2006. Mammalian PGRPs: novel antibacterial proteins. Cell Microbiol. 8:1059-1069.
15. Ebensen, T., et al., Bacterial ghosts are an efficient delivery system for DNA vaccines. J Immunol, 2004. 172(11): p. 6858-65.
16. Eko, F. O., T. Schukovskaya, E. Y. Lotzmanova, V. V. Firstova, N. V. Emalyanova, S. N. Klueva, A. L. Kravtzov, L. F. Livanova, V. V. Kutyrev, J. U. lgietseme, and W. Lubitz. 2003. Evaluation of the protective efficacy of *Vibrio cholerae* ghost (VCG) candidate vaccines in rabbits. Vaccine 21:3663-3674.
17. Faith, S. A., et al., Resveratrol suppresses nuclear factor-kappaB in herpes simplex virus infected cells. Antiviral Res, 2006. 72(3): p. 242-51.
18. Falchetti, R., et al., Effects of resveratrol on human immune cell function. Life Sci, 2001. 70(1): p. 81-96.
19. Gao, X., et al., Immunomodulatory activity of resveratrol: discrepant in vitro and in vivo immunological effects. Biochem Pharmacol, 2003. 66(12): p. 2427-35.
20. Glaser, R., J. Harder, H. Lange, J. Bartels, E. Christophers, and J. M. Schroder. 2005. Antimicrobial psoriasin (S100A7) protects human skin from *Escherichia coli* infection. Natl. Immunol. 6:57-64.
21. Green, L. C., et al., Analysis of nitrate, nitrite, and [15N] nitrate in biological fluids. Anal Biochem, 1982. 126(1): p. 131-8.
22. Harder, J. and G. Nunez. 2009. Functional Expression of the Intracellular Pattern Recognition Receptor NOD1 in Human Keratinocytes. J. Invest Dermatol. 5:1299-302
23. Haslberger, A. G., et al., Activation, stimulation and uptake of bacterial ghosts in antigen presenting cells. J Biotechnol, 2000. 83(1-2): p. 57-66.
24. Hayashi, F., K. D. Smith, A. Ozinsky, T. R. Hawn, E. C. Yi, D. R. Goodlett, J. K. Eng, S. Akira, D. M. Underhill, and A. Aderem. 2001. The innate immune response to bacterial flagellin is mediated by Toll-like receptor 5. Nature 410: 1099-1103.
25. Hirohashi, N. and D. C. Morrison, Low-dose lipopolysaccharide (LPS) pretreatment of mouse macrophages modulates LPS-dependent interleukin-6 production in vitro. Infect Immun, 1996. 64(3): p. 1011-5.
26. Huter, V., M. P. Szostak, J. Gampfer, S. Prethaler, G. Wanner, F. Gabor, and W. Lubitz. 1999. Bacterial ghosts as drug carrier and targeting vehicles. Journal of Controlled Release 61:51-63.
27. Ishii, K. J., S. Koyama, A. Nakagawa, C. Coban, and S. Akira. 2008. Host innate immune receptors and beyond: making sense of microbial infections. Cell Host. Microbe 3:352-363.
28. Jalava, K., F. O. Eko, E. Riedmann, and W. Lubitz. 2003. Bacterial ghosts as carrier and targeting systems for mucosal antigen delivery. Expert. Rev. Vaccines. 2:45-51.
29. Jechlinger, W., C. Haller, S. Resch, A. Hofmann, M. P. Szostak, and W. Lubitz. 2005. Comparative immunogenicity of the hepatitis B virus core 149 antigen displayed on the inner and outer membrane of bacterial ghosts. Vaccine 23:3609-3617.
30. Kedzierski, L., et al., In vitro antileishmanial activity of resveratrol and its hydroxylated analogues against *Leishmania major* promastigotes and amastigotes. Parasitol Res, 2007. 102(1): p. 91-7.
31. Kedzierski, L., et al., Leishmaniasis: current treatment and prospects for new drugs and vaccines. Curr Med Chem, 2009. 16(5): p. 599-614.
32. Kudela, P., S. Paukner, U. B. Mayr, D. Cholujova, G. Kohl, Z. Schwarczova, J. Bizik, J. Sedlak, and W. Lubitz. 2007. Effective gene transfer to melanoma cells using bacterial ghosts. Cancer Lett. 1:54-63
33. Kudela, P., S. Paukner, U. B. Mayr, D. Cholujova, Z. Schwarczova, J. Sedlak, J. Bizik, and W. Lubitz. 2005. Bacterial ghosts as novel efficient targeting vehicles for DNA delivery to the human monocyte-derived dendritic cells. J. Immunother. 28:136-143.
34. Leiro, J., et al., In vitro effects of resveratrol on the viability and infectivity of the microsporidian *Encephalitozoon cuniculi*. Antimicrob Agents Chemother, 2004. 48(7): p. 2497-501.
35. Leiro, J., et al., In vitro effects of the polyphenols resveratrol, mangiferin and (−)-epigallocatechin-3-gallate on the scuticociliate fish pathogen Philasterides dicentrarchi. Dis Aquat Organ, 2004. 59(2): p. 171-4.
36. Lin, H. Y., et al., Integrin alphaVbeta3 contains a receptor site for resveratrol. Faseb J, 2006. 20(10): p. 1742-4.
37. Lubitz, P., U. B. Mayr, and W. Lubitz. 2009. Applications of Bacterial Ghosts in Biomedicine, In: C. A. Guzman and G. Feuerstein (eds.), Pharmaceutical Biotechnology. Landes Biosciences, Austin, Tex., USA.
38. Mader, H. J., et al., Endotoxicity does not limit the use of bacterial ghosts as candidate vaccines. Vaccine, 1997. 15(2): p. 195-202.

39. Mayr, U. B., P. Walcher, C. Azimpour, E. Riedmann, C. Haller, and W. Lubitz. 2005. Bacterial ghosts as antigen delivery vehicles. Adv. Drug Deliv. Rev. 57:1381-1391.
40. Mayr, U. B., et al., Bacterial ghosts as an oral vaccine: a single dose of *Escherichia coli* 0157:H7 bacterial ghosts protects mice against lethal challenge. Infect Immun, 2005. 73(8): p. 4810-7.
41. Mildner, M., C. Ballaun, M. Stichenwirth, R. Bauer, R. Gmeiner, M. Buchberger, V. Mlitz, and E. Tschachler. 2006. Gene silencing in a human organotypic skin model. Biochem. Biophys. Res. Commun. 348:76-82.
42. Miller, L. S., O. E. Sorensen, P. T. Liu, H. R. Jalian, D. Eshtiaghpour, B. E. Behmanesh, W. Chung, T. D. Starner, J. Kim, P. A. Sieling, T. Ganz, and R. L. Modlin. 2005. TGF-alpha regulates TLR expression and function on epidermal keratinocytes. J. Immunol. 174:6137-6143.
43. Panaro, M. A., et al., Inducible nitric oxide synthase and nitric oxide production in *Leishmania infantum*-infected human macrophages stimulated with interferon-gamma and bacterial lipopolysaccharide. Int J Clin Lab Res, 1999. 29(3): p. 122-7.
44. Paukner, S., et al., Sealed bacterial ghosts—novel targeting vehicles for advanced drug delivery of water-soluble substances. J Drug Target, 2003. 11(3): p. 151-61.
45. Paukner, S., T. Stiedl, P. Kudela, J. Bizik, F. Al Laham, and W. Lubitz. 2006. Bacterial ghosts as a novel advanced targeting system for drug and DNA delivery. Expert. Opin. Drug Deliv. 3:11-22.
46. Pfaffl, M. W. 2001. A new mathematical model for relative quantification in real-time RT-PCR. Nucleic Acids Res. 29:e45.
47. Rendl, M., J. Ban, P. Mrass, C. Mayer, B. Lengauer, L. Eckhart, W. Declerq, and E. Tschachler. 2002. Caspase-14 expression by epidermal keratinocytes is regulated by retinoids in a differentiation-associated manner. J. Invest Dermatol. 119:1150-1155.
48. Repetto, G., A. del Peso, and J. L. Zurita, Neutral red uptake assay for the estimation of cell viability/cytotoxicity. Nat Protoc, 2008. 3(7): p. 1125-31.
49. Riedmann, E. M., J. M. Kyd, A. W. Cripps, and W. Lubitz. 2007. Bacterial ghosts as adjuvant particles. Expert. Rev. Vaccines. 6:241-253.
50. Saiko, P., et al., Resveratrol and its analogs: defense against cancer, coronary disease and neurodegenerative maladies or just a fad? Mutat Res, 2008. 658(1-2): p. 68-94.
51. Schriever, C., S. L. Pendland, and G. B. Mahady, Red wine, resveratrol, *Chlamydia pneumoniae* and the French connection. Atherosclerosis, 2003. 171(2): p. 379-80.
52. Sharma, J. N., A. Al-Omran, and S. S. Parvathy, Role of nitric oxide in inflammatory diseases. Inflammopharmacology, 2007. 15(6): p. 252-9.
53. Summersgill, J. T., et al., Killing of *Legionella pneumophila* by nitric oxide in gamma-interferon-activated macrophages. J Leukoc Biol, 1992. 52(6): p. 625-9.
54. Tsai, S. H., S. Y. Lin-Shiau, and J. K. Lin, Suppression of nitric oxide synthase and the down-regulation of the activation of NFkappaB in macrophages by resveratrol. Br J Pharmacol, 1999. 126(3): p. 673-80.
55. Udenigwe, C. C., et al., Potential of resveratrol in anti-cancer and anti-inflammatory therapy. Nutr Rev, 2008. 66(8): p. 445-54.
56. Viala, J., C. Chaput, I. G. Boneca, A. Cardona, S. E. Girardin, A. P. Moran, R. Athman, S. Memet, M. R. Huerre, A. J. Coyle, P. S. DiStefano, P. J. Sansonetti, A. Labigne, J. Bertin, D. J. Philpott, and R. L. Ferrero. 2004. Nod1 responds to peptidoglycan delivered by the *Helicobacter pylori* cag pathogenicity island. Nat. Immunol. 5:1166-1174.
57. Voss, E., J. Wehkamp, K. Wehkamp, E. F. Stange, J. M. Schroder, and J. Harder. 2006. NOD2/CARD15 mediates induction of the antimicrobial peptide human beta-defensin-2. J. Biol. Chem. 281:2005-2011
58. Witte, A., et al., Dynamics of PhiX174 protein E-mediated lysis of *Escherichia coli*. Arch Microbiol, 1992. 157(4): p. 381-8.
59. Witte, A., G. Wanner, U. Blasi, G. Halfmann, M. Szostak, and W. Lubitz. 1990. Endogenous transmembrane tunnel formation mediated by phi X174 lysis protein E. J. Bacteriol. 172:4109-4114.
60. Witte, A., G. Wanner, W. Lubitz, and J. V. Holtje. 1998. Effect of phi X174 protein E-mediated lysis on murein composition of *Escherichia coil*. FEMS Microbiol. Lett. 164:149-157.
61. Witte, A., U. Blasi, G. Halfmann, M. Szostak, G. Wanner, and W. Lubitz. 1990. Phi X174 protein E-mediated lysis of *Escherichia coli*. Biochimie 72:191-200.

The invention claimed is:

1. A method of promoting an innate immune response in a patient in need thereof, comprising:
   administering to said patient bacterial ghosts (BG) in an effective amount to produce an innate immune response,
   wherein the innate immune response is promoted by induction of the expression and/or release of at least one innate immune modulator,
   wherein the expression of at least one antimicrobial defense molecule is enhanced in said patient compared to the expression of said antimicrobial defense molecule before administration of said effective amount of bacterial ghosts,
   wherein the bacterial ghosts are derived from *E. coli* Nissle 1917.

2. The method of claim 1, wherein the surface of the bacterial ghosts does not comprise flagellin monomers.

3. The method of claim 1, wherein the surface of the bacterial ghosts does not comprise flagellin.

4. The method of claim 1, wherein the expression and/or release of at least one innate immune modulator is induced in epithelial cells.

5. The method of claim 4, wherein the epithelial cells are keratinocytes.

6. The method of claim 1, wherein the at least one innate immune modulator is selected from the group consisting of antimicrobial defense molecules, pro-inflammatory cytokines, reactive nitrogen species (RNS) and reactive oxygen species (ROS).

7. The method of claim 1, wherein the at least one antimicrobial defense molecule is selected from the group consisting of psoriasin and human β defensin-2 (hBD-2).

8. The method of claim 1, wherein the expression and/or release of at least one pro-inflammatory cytokine is enhanced.

9. The method of claim 8, wherein the at least one pro-inflammatory cytokine is selected from the group consisting of interleukin-6 (IL-6) and interleukin-8 (IL-8).

10. The method of claim 1, wherein the release of at least one reactive nitrogen species (RNS) is enhanced.

11. The method of claim 10, wherein the reactive nitrogen species is NO.

12. The method of claim 1, wherein the innate immune response is promoted in mammals.

13. The method of claim 1, wherein the bacterial ghosts are administered in combination with a further active agent.

14. The method of claim 13, wherein the active agent is resveratrol.

15. The method of claim 1, wherein the bacterial ghosts are administered to the skin and/or mucosa.

16. The method of claim 1, wherein the bacterial ghosts are administered orally, topically, mucosally, pulmonally and/or nasally.

17. The method of claim 1, wherein the bacterial ghosts are administered to individuals with compromised immune system.

18. The method of claim 1, wherein said patient is a human.

* * * * *